US 7,476,196 B2

(12) United States Patent
Spence et al.

(10) Patent No.: US 7,476,196 B2
(45) Date of Patent: Jan. 13, 2009

(54) DEVICE TO PERMIT OFFPUMP BEATING HEART CORONARY BYPASS SURGERY

(75) Inventors: Paul A. Spence, Louisville, KY (US); Warren P. Williamson, IV, Loveland, OH (US); Mark Ortiz, Milford, OH (US)

(73) Assignee: MAQUET Cardiovascular, LLC, San Jose, CA (US)

( * ) Notice: Subject to any disclaimer, the term of this patent is extended or adjusted under 35 U.S.C. 154(b) by 956 days.

(21) Appl. No.: 10/863,409

(22) Filed: Jun. 8, 2004

(65) Prior Publication Data

US 2004/0225195 A1 Nov. 11, 2004

Related U.S. Application Data

(63) Continuation of application No. 10/698,798, filed on Oct. 31, 2003, now Pat. No. 7,377,895, which is a continuation of application No. 09/956,418, filed on Sep. 18, 2001, now Pat. No. 6,743,170, which is a continuation of application No. 09/087,511, filed on May 29, 1998, now Pat. No. 6,338,712, which is a continuation-in-part of application No. 08/936,184, filed on Sep. 17, 1997, now Pat. No. 6,019,722.

(51) Int. Cl.
*A61B 19/00* (2006.01)

(52) U.S. Cl. ....................................... 600/37

(58) Field of Classification Search ................ 600/37, 600/201, 210, 228, 229, 231, 232, 235
See application file for complete search history.

(56) References Cited

U.S. PATENT DOCUMENTS 452,131 A 5/1891 Haughawout (Continued)

FOREIGN PATENT DOCUMENTS

DE 3138589 A1 4/1983

(Continued)

OTHER PUBLICATIONS

C.W. Akins et al., "Preservation of Interventricular Septal Function in Patients Having Coronary Artery Bypass Grafts Without Cardiopulmonary Bypass," American Heart Journal, vol. 107, No. 2, Feb. 1984, pp. 304-309.

(Continued)

*Primary Examiner*—Samuel G Gilbert
(74) *Attorney, Agent, or Firm*—Alan W. Cannon

(57) ABSTRACT

A suction cup adapted to engage a surface of a beating heart with sufficient force to move the beating heart to an unnatural position upon moving the suction cup, while the suction cup maintains engagement with the surface of the heart and the heart continues to beat. Various suction cups are described each including at least a first chamber having a flexible rim and configured to engage the surface of the beating heart and a second chamber smaller than the first chamber and fluidly connected therewith. A suspension device configured to engage a beating heart and maintain engagement via suction while moving the suspension device to move the beating heart to an unnatural position and maintain the beating heart in the unnatural position to perform a surgical procedure, while the heart continues to beat, includes a suction cup and a support arm connected thereto. The suction cup has a first chamber configured to engage the surface of the beating heart, and a second chamber smaller than the first chamber and fluidly connected therewith. The second chamber is adapted to fluidly connect the first chamber with a source of suction. The support arm is movable with the suction cup to effect movement of the beating heart after engagement of the suction cup to a surface of the beating heart. A method of manipulating a beating heart to orient the beating heart in a desired position for performing a surgical procedure includes providing a suction cup having a first chamber configured to engage the surface of the beating heart, and a second chamber smaller than the first chamber and fluidly connected with the first chamber, the second chamber being further fluidly connected to a source of suction; contacting a surface of the beating heart with the first chamber; applying suction between the first chamber and the surface of the beating heart, thereby engaging the suction member with the surface of the beating heart; and moving the suction member while maintaining engagement with the surface of the beating heart, thereby moving the beating heart.

48 Claims, 11 Drawing Sheets

U.S. PATENT DOCUMENTS

| | | |
|---|---|---|
| 810,675 A | 1/1906 | Richter |
| 1,706,500 A | 3/1929 | Smith |
| 2,082,782 A | 6/1937 | Allen |
| 2,296,793 A | 9/1942 | Kirschbaum |
| 2,590,527 A | 3/1952 | Fluck |
| 2,693,795 A | 11/1954 | Grieshaber |
| 2,863,444 A | 12/1958 | Winsten |
| 3,361,133 A | 1/1968 | Kimberley et al. |
| 3,392,722 A | 7/1968 | Jorgensen |
| 3,466,079 A | 9/1969 | Mammel |
| 3,584,822 A | 6/1971 | Oram |
| 3,683,926 A | 8/1972 | Suzuki |
| 3,720,433 A | 3/1973 | Rosfelder |
| 3,783,873 A | 1/1974 | Jacobs |
| 3,807,406 A | 4/1974 | Rafferty et al. |
| 3,858,926 A | 1/1975 | Ottenhues |
| 3,882,855 A | 5/1975 | Shulte et al. |
| 3,912,317 A | 10/1975 | Ohnaka |
| 3,916,909 A | 11/1975 | Kletschka et al. |
| 3,983,863 A | 10/1976 | Janke et al. |
| 4,047,532 A | 9/1977 | Phillips et al. |
| 4,048,987 A | 9/1977 | Hurson |
| 4,049,000 A | 9/1977 | Williams |
| 4,049,002 A | 9/1977 | Kletschka et al. |
| 4,049,484 A | 9/1977 | Priest et al. |
| 4,052,980 A | 10/1977 | Grams et al. |
| 4,094,484 A | 6/1978 | Galione |
| 4,096,853 A | 6/1978 | Weigand |
| 4,096,864 A | 6/1978 | Kletschka et al. |
| 4,217,890 A | 8/1980 | Owens |
| 4,226,228 A | 10/1980 | Shin et al. |
| 4,230,119 A | 10/1980 | Blum |
| 4,300,564 A | 11/1981 | Furihata |
| 4,306,561 A | 12/1981 | de Medinaceli |
| 4,350,160 A | 9/1982 | Kolesov et al. |
| 4,366,819 A | 1/1983 | Kaster |
| 4,368,736 A | 1/1983 | Kaster |
| 4,421,107 A | 12/1983 | Estes et al. |
| 4,428,368 A | 1/1984 | Torii |
| 4,434,791 A | 3/1984 | Darnell |
| 4,457,300 A | 7/1984 | Budde |
| 4,461,284 A | 7/1984 | Fackler |
| 4,492,229 A | 1/1985 | Grunwald |
| 4,617,916 A | 10/1986 | LeVahn et al. |
| 4,627,421 A | 12/1986 | Symbas et al. |
| 4,637,377 A | 1/1987 | Loop |
| 4,646,747 A | 3/1987 | Lundback |
| 4,688,570 A | 8/1987 | Kramer et al. |
| 4,702,230 A | 10/1987 | Pelta |
| D293,470 S | 12/1987 | Adler |
| 4,718,418 A | 1/1988 | L'Esperance, Jr. |
| 4,726,356 A | 2/1988 | Santilli et al. |
| 4,726,358 A | 2/1988 | Brady |
| 4,736,749 A | 4/1988 | Lundback |
| 4,747,395 A | 5/1988 | Brief |
| 4,754,746 A | 7/1988 | Cox |
| 4,803,984 A | 2/1989 | Narayanan et al. |
| 4,808,163 A | 2/1989 | Laub |
| 4,827,926 A | 5/1989 | Carol |
| 4,829,985 A | 5/1989 | Couetil |
| 4,841,967 A | 6/1989 | Chang et al. |
| 4,852,552 A | 8/1989 | Chaux |
| 4,854,318 A | 8/1989 | Solem et al. |
| 4,858,552 A | 8/1989 | Glatt et al. |
| 4,863,133 A | 9/1989 | Bonnell |
| 4,865,019 A | 9/1989 | Phillips |
| 4,884,559 A | 12/1989 | Collins |
| 4,904,012 A | 2/1990 | Nishiguchi et al. |
| 4,917,427 A * | 4/1990 | Scaglia .................. 294/64.1 |
| 4,925,443 A | 5/1990 | Heilman et al. |
| 4,949,707 A | 8/1990 | LeVahn et al. |
| 4,949,927 A | 8/1990 | Madocks et al. |
| 4,955,896 A | 9/1990 | Freeman |
| 4,957,477 A | 9/1990 | Lundback |
| 4,962,758 A | 10/1990 | Lasner et al. |
| 4,971,037 A | 11/1990 | Pelta |
| 4,973,300 A | 11/1990 | Wright |
| 4,989,587 A | 2/1991 | Farley |
| 4,991,578 A | 2/1991 | Cohen |
| 4,993,862 A | 2/1991 | Pelta |
| 5,009,660 A | 4/1991 | Clapham |
| 5,011,469 A | 4/1991 | Buckberg et al. |
| 5,019,086 A | 5/1991 | Neward |
| 5,025,779 A | 6/1991 | Bugge |
| 5,036,868 A | 8/1991 | Berggren et al. |
| 5,037,428 A | 8/1991 | Picha et al. |
| 5,052,373 A | 10/1991 | Michelson |
| 5,053,041 A | 10/1991 | Ansari et al. |
| 5,080,088 A | 1/1992 | LeVahn |
| 5,098,369 A | 3/1992 | Heilman et al. |
| 5,119,804 A | 6/1992 | Anstadt |
| 5,125,395 A | 6/1992 | Adair |
| 5,131,905 A | 7/1992 | Grooters |
| 5,133,724 A | 7/1992 | Wilson, Jr. et al. |
| 5,139,517 A | 8/1992 | Corral |
| 5,150,706 A | 9/1992 | Cox et al. |
| 5,152,777 A | 10/1992 | Goldberg et al. |
| 5,159,921 A | 11/1992 | Hoover |
| RE34,150 E | 12/1992 | Santilli et al. |
| 5,167,223 A | 12/1992 | Koros et al. |
| 5,171,254 A | 12/1992 | Sher |
| 5,192,070 A | 3/1993 | Nagai et al. |
| 5,196,003 A | 3/1993 | Bilweis |
| 5,231,974 A | 8/1993 | Giglio et al. |
| 5,256,132 A | 10/1993 | Snyders |
| 5,268,640 A | 12/1993 | Du et al. |
| 5,287,861 A | 2/1994 | Wilk |
| 5,290,082 A | 3/1994 | Palmer et al. |
| 5,293,863 A | 3/1994 | Zhu et al. |
| 5,300,087 A | 4/1994 | Knoepfler |
| 5,318,013 A | 6/1994 | Wilk |
| 5,336,252 A | 8/1994 | Cohen |
| 5,348,259 A | 9/1994 | Blanco et al. |
| 5,363,882 A | 11/1994 | Chikama |
| 5,382,756 A | 1/1995 | Dagan |
| 5,383,840 A | 1/1995 | Heilman et al. |
| 5,417,709 A | 5/1995 | Slater |
| 5,425,705 A | 6/1995 | Evard et al. |
| 5,437,651 A | 8/1995 | Todd et al. |
| 5,452,733 A | 9/1995 | Sterman et al. |
| 5,453,078 A | 9/1995 | Valentine et al. |
| 5,467,763 A | 11/1995 | McMahon et al. |
| 5,480,425 A | 1/1996 | Ogilive |
| 5,484,391 A | 1/1996 | Buckman, Jr. et al. |
| 5,498,256 A | 3/1996 | Furnish |
| 5,503,617 A | 4/1996 | Jako |
| 5,509,890 A | 4/1996 | Kazama |
| 5,512,037 A | 4/1996 | Russell et al. |
| 5,514,075 A | 5/1996 | Moll et al. |
| 5,514,076 A | 5/1996 | Ley |
| 5,520,610 A | 5/1996 | Giglio et al. |
| 5,522,819 A | 6/1996 | Graves et al. |
| 5,529,571 A | 6/1996 | Daniel |
| 5,536,251 A | 7/1996 | Evard et al. |
| 5,547,458 A | 8/1996 | Ortiz et al. |
| 5,569,274 A | 10/1996 | Rapacki et al. |
| 5,571,074 A | 11/1996 | Buckman, Jr. et al. |
| 5,571,215 A | 11/1996 | Sterman et al. |
| 5,573,496 A | 11/1996 | McPherson et al. |
| 5,582,580 A | 12/1996 | Buckman, Jr. et al. |
| 5,607,421 A | 3/1997 | Jeevanandam et al. |
| 5,607,446 A | 3/1997 | Beehler et al. |
| 5,613,937 A | 3/1997 | Garrison et al. |
| 5,632,746 A | 5/1997 | Middleman et al. |

| | | |
|---|---|---|
| 5,651,378 A | 7/1997 | Matheny et al. |
| 5,662,300 A | 9/1997 | Michelson |
| 5,667,480 A | 9/1997 | Knight et al. |
| 5,713,951 A | 2/1998 | Garrison et al. |
| 5,727,569 A | 3/1998 | Benetti et al. |
| 5,728,151 A | 3/1998 | Garrison et al. |
| 5,730,757 A | 3/1998 | Benetti et al. |
| 5,735,290 A | 4/1998 | Sterman et al. |
| 5,749,892 A | 5/1998 | Vierra et al. |
| 5,755,660 A | 5/1998 | Tyagi |
| 5,766,151 A | 6/1998 | Valley et al. |
| 5,772,583 A | 6/1998 | Wright et al. |
| 5,782,746 A * | 7/1998 | Wright ............... 600/37 |
| 5,795,291 A | 8/1998 | Koros et al. |
| 5,797,960 A | 8/1998 | Stevens et al. |
| 5,799,661 A * | 9/1998 | Boyd et al. ............ 128/898 |
| 5,807,243 A | 9/1998 | Vierra et al. |
| 5,813,410 A | 9/1998 | Levin |
| 5,818,231 A | 10/1998 | Smith |
| 5,836,311 A | 11/1998 | Borst et al. |
| 5,864,275 A | 1/1999 | Ohashi et al. |
| 5,865,730 A | 2/1999 | Fox et al. |
| 5,885,271 A | 3/1999 | Hamilton et al. |
| 5,888,247 A | 3/1999 | Benetti |
| 5,891,017 A | 4/1999 | Swindle et al. |
| 5,894,843 A | 4/1999 | Benetti et al. |
| 5,899,425 A | 5/1999 | Corey Jr. et al. |
| 5,906,607 A | 5/1999 | Taylor et al. |
| 5,908,378 A | 6/1999 | Kovacs et al. |
| 5,921,979 A | 7/1999 | Kovacs et al. |
| 5,927,284 A | 7/1999 | Borst et al. |
| 5,947,896 A | 9/1999 | Sherts et al. |
| 5,957,835 A | 9/1999 | Anderson et al. |
| 5,967,973 A | 10/1999 | Sherts et al. |
| 5,976,069 A | 11/1999 | Navia et al. |
| 5,976,080 A | 11/1999 | Farascioni et al. |
| 5,984,864 A * | 11/1999 | Fox et al. ............... 600/201 |
| 6,013,027 A | 1/2000 | Khan et al. |
| 6,015,378 A | 1/2000 | Borst et al. |
| 6,015,427 A | 1/2000 | Mueller et al. |
| 6,019,722 A | 2/2000 | Spence et al. |
| 6,032,672 A | 3/2000 | Taylor |
| 6,033,362 A | 3/2000 | Cohn |
| 6,036,641 A | 3/2000 | Taylor et al. |
| 6,042,539 A | 3/2000 | Harper et al. |
| 6,110,187 A | 8/2000 | Donlon |
| 6,139,492 A | 10/2000 | Vierra et al. |
| 6,149,583 A | 11/2000 | Vierra et al. |
| 6,159,201 A | 12/2000 | Hamilton et al. |
| 6,183,486 B1 | 2/2001 | Snow et al. |
| 6,210,323 B1 | 4/2001 | Gilhuly et al. |
| 6,213,940 B1 | 4/2001 | Sherts et al. |
| 6,231,585 B1 | 5/2001 | Takahashi et al. |
| 6,251,065 B1 | 6/2001 | Kochamba |
| 6,264,605 B1 | 7/2001 | Scirica et al. |
| 6,315,717 B1 | 11/2001 | Benetti et al. |
| 6,328,688 B1 | 12/2001 | Borst et al. |
| 6,334,843 B1 | 1/2002 | Borst et al. |
| 6,336,898 B1 | 1/2002 | Borst et al. |
| 6,338,712 B2 | 1/2002 | Spence et al. |
| 6,346,077 B1 | 2/2002 | Taylor et al. |
| 6,350,229 B1 | 2/2002 | Borst et al. |
| 6,361,493 B1 | 3/2002 | Spence et al. |
| 6,364,826 B1 | 4/2002 | Borst et al. |
| 6,371,906 B1 | 4/2002 | Borst et al. |
| 6,371,910 B1 | 4/2002 | Zwart et al. |
| 6,375,611 B1 | 4/2002 | Voss et al. |
| 6,390,976 B1 | 5/2002 | Spence et al. |
| 6,394,948 B1 | 5/2002 | Borst et al. |
| 6,394,951 B1 | 5/2002 | Taylor et al. |
| 6,398,726 B1 | 6/2002 | Romans et al. |
| 6,406,424 B1 | 6/2002 | Williamson et al. |
| 6,447,443 B1 | 9/2002 | Keogh et al. |
| 6,458,079 B1 | 10/2002 | Cohn et al. |
| 6,464,629 B1 | 10/2002 | Boone et al. |
| 6,464,630 B1 | 10/2002 | Borst et al. |
| 6,468,265 B1 | 10/2002 | Evans et al. |
| 6,478,029 B1 | 11/2002 | Boyd et al. |
| 6,478,729 B1 | 11/2002 | Rogers et al. |
| 6,482,151 B1 | 11/2002 | Vierra et al. |
| 6,494,211 B1 | 12/2002 | Boyd et al. |
| 6,503,245 B2 | 1/2003 | Palmer et al. |
| 6,506,149 B2 | 1/2003 | Peng et al. |
| 6,537,212 B2 | 3/2003 | Sherts et al. |
| 6,565,508 B2 | 5/2003 | Scirica et al. |
| 6,589,166 B2 | 7/2003 | Knight et al. |
| 6,592,573 B2 | 7/2003 | Castaneda |
| 6,607,479 B1 | 8/2003 | Kochamba et al. |
| 6,610,008 B1 | 8/2003 | Spence et al. |
| 6,610,009 B2 | 8/2003 | Person |

FOREIGN PATENT DOCUMENTS

| | | |
|---|---|---|
| DE | 9004513 | 6/1990 |
| DE | 4139695 A1 | 6/1993 |
| EP | 0 293 760 A2 | 12/1988 |
| EP | 0 293 760 A3 | 12/1988 |
| EP | 0 293 760 B1 | 12/1988 |
| EP | 0 630 629 A1 | 5/1994 |
| EP | 0 668 058 A1 | 2/1995 |
| EP | 668 058 A1 | 8/1995 |
| EP | 0 791 330 A2 | 2/1997 |
| EP | 0 820 721 A1 | 7/1997 |
| EP | 0 791 329 A1 | 8/1997 |
| EP | 0 808 606 A1 | 11/1997 |
| EP | 0 820 721 A1 | 1/1998 |
| EP | 0 919 193 A1 | 2/1999 |
| GB | 168216 | 9/1921 |
| GB | 2 233 561 A | 1/1991 |
| GB | 2 267 827 A | 12/1993 |
| SU | 938967 | 7/1982 |
| WO | WO 87/04081 | 7/1987 |
| WO | WO 88/00481 | 1/1988 |
| WO | WO 94/14383 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 96/40354 | 12/1996 |
| WO | WO 97/10753 | 3/1997 |
| WO | WO 97/26828 A | 7/1997 |
| WO | WO 97/40752 | 11/1997 |
| WO | WO 98/37814 | 9/1998 |
| WO | WO 98/49944 | 11/1998 |
| WO | WO 99/60929 | 12/1999 |
| WO | WO 99/60930 | 12/1999 |
| WO | WO 00/10466 | 3/2000 |
| WO | WO 01/58362 A1 | 8/2001 |

OTHER PUBLICATIONS

Ancalmo, N. and J. L. Ochsner: "A Modified Sternal Retractor," Ann. Thorac, Surg. 21 (1976) 174.

Angelini, G.D., M.D. et al., "A Fiber-Optic Retractor for Harvesting the Internal Mammary Artery," Ann. Thorac. Surg. (1990; 50:314-5).

Angelini, G.D., M.D., "A Simple, Inexpensive Method of Heart Retraction During Coronary Artery Bypass Surgery," Ann. Thora. Surg 46:46-247, Aug. 1988.

Anstadt, M.P. MD et al., "Direct Mechanical Ventricular Actuation for Cardiac Arrest in Humans," Chest, vol. 100, No. 1, Jul. 1991, pp. 86-92.

Antinori, C. et al., "A Method of Retraction During Reoperative Coronary Operations Using the Favaloro Retractor," The Society of Thoracic Surgeons: 1989.

Archer, R. Do et al., "Coronary Artery Revascularization Without Cardiopulmonary Bypass," Texas Heart Institute Journal, vol. 11, No. 1, Mar. 1984, pp. 52-57.

Arom, K. V., et al., "Mini-Sternotomy for Coronary Artery Bypass Grafting," The Annals of Thoracic Surgery 1996; 61:1271-2.

Ballantyne, C.M. et al. "Delayed Recovery of Severely 'Stunned' Myocardium With the Support of a Left Ventricular Assist Device after Coronary Artery Bypass Graft Surgery," Journal of the American College of Cardiology, vol. 10, No. 3, Sep. 1987, pp. 710-712.

Bedellino, M.M., et al., "The Cardiac Rag—Simple Exposure of the Heart," Texas Heart Institute Journal, vol. 15, No. 2, 1988, 134-35.

Beg, R.A. et al., "Internal Mammary Retractor," Ann Thorac, Surg., vol. 39, No. 1, Jan. 1985, pp. 286-287.

Benetti, F. J. et al., "Direct Coronary Surgery with Saphenous Vein Bypass Without Either Cardiopulmonary Bypass Graft or Cardiac Arrest," The Journal of Cardiovascular Surgery, vol. 26, No. 3, May-Jun. 1985, pp. 217-222.

Benetti, F. J. et al., "Direct Myocardial Revascularization Without Extracorporeal Circulation," Chest, vol. 100, No. 2, Aug. 1991, pp. 312-316.

Benetti, F. J., "Coronary Revascularization with Arterial Conduits via a Small Thoracotomy and Assisted by Thoracoscopy, Although Without Cardiopulmonary Bypass," Cor Europaeum 4 (1) 22-24 (1995).

Borst et al., "Coronary Artery Bypass Grafting Without Cardiopulmonary Bypass and Without Interruption of Native Coronary Flow Using a Novel Anastomosis Site Restraining Device ('Octopus')", JAAC vol. 27, No. 6, May 1996:1356-64.

C. Borst et al., entitled "Regional Cardiac Wall Immunobilization for Open Chest and Closed Chest Coronary Artery Bypass Grafting on the Beating Heart: The 'Octopus' Method," Circulation, (Oct. 15, 1995) vol. 92, No. 8 supplemental I,I-177.

Bugge, M., "A New Internal Mammary Artery Retractor," Thorac. Cardiovasc Surgeon 38, pp. 316-317 (1990).

Buffolo, E., et al., "Direct Myocardial Revascularization Without Cardiopulmonary Bypass," Thorac. Cardiovasc. Surgeon, 33 (1985) pp. 26-29.

Calafiore, A. M., et al., "Minimally Invasive Coronary Artery Bypass Grafting," The Annals of Thoracic Surgery, 62:1545-8, 1996.

Calvin, I. F. & Newman, D.C., "Circumflex Exposure Using a Cardiac Sling," Ann Thorac Surg 1990:49:833-4.

Campalani, G., M.D., et al., "A New Self-Retaining Internal Mammary Artery Retractor," J. Cardiovas. Surg. 28, 1987, pp. 347-348.

Chaux, A. and Blanche, C., "A New Concept in Sternal Retraction: Applications for Internal Mammary Artery Dissection and Valve Replacement Surgery," Ann. Thorac. Surg. 42, Oct. 1986, pp. 473-474.

Cohen, A.S., et al., "Mini-Sternotomy for Coronary Artery Bypass Grafting," The Annals of Thoracic Surgery 1996; 62:1884-85.

Cutler, B.S. and Cantelmo, N.L., "New Use for an Old Clamp," Archives of Surgery—vol. 115, 1136-37, Sep. 1980.

DelRossi, A J and Lemole, GM, "A New Retractor to Aid in Coronary Artery Surgery," The Annals of Thoracic Surgery, vol. 36, No. 1, 101-102, Jul. 1983.

Fanning, W. J. et al., "Reoperative Coronary Artery Bypass Grafting Without Cardiopulmonary Bypass," The Annals of Thoracic Surgery, vol. 55, No. 2, Feb. 1993, pp. 486-489.

Favaloro, R. G., et al. "Direct Myocardial Revascularization by Saphenous Vein Graft," The Annals of Thoracic Surgery, vol. 10, No. 2, Aug. 1970, pp. 97-111.

Fonger, J. D., et al., "Enhanced Preservation of Acutely Ischmenic Myocardium with Transeptal Left Ventricular Assist," The Annals of Thoracic Surgery, vol. 57, No. 3, Mar. 1994, pp. 570-575.

Gacioch, G. M., MD, et al., "Cardiogenic Shock Complicating Acute Myocardial Infarction: The Use of Coronary Angioplasty and the Integration of the New Support Device into Patient Management," Journal of the American College of Cardiology, vol. 19, No. 3, Mar. 1, 1992.

Green, GE., "Technique of Internal Mammary-Coronary Artery Anastomosis," The Journal of Cardiovascular Surgery, 78:455-79, 1979.

Grundeman et al., "Vertical Displacement of the Beating Heart by the Octopus Tissue Stabilizer: Influence on Coronary Flow", Ann Thorac Surg 1998; 65: 138-152.

Grundeman et al., "Hemodynamic Changes During Displacement of the Beating Heart by the Utrecht Octopus Method", Ann Thorac Surg 1997; 66:576-579.

Guzman, F. M.D., "Transient Radial Nerve Injury Related to the Use of A Self Retraining Retractor for Internal Mammary Artery Dissection," J. Cardiovasc. Surg. 30, 1989, pp. 1015-1016.

Hasan, R. I., et al., "Technique of Dissecting the Internal Mammary After Using The Moussalli Bar," European Journal of Cardio Thoracic Surgery, 4:571-572, 1990.

Itoh, Toshiaki, M.D., et al., "New Modification of a Mammary Artery Retractor," Ann. Thorac. Surg. 9, 1994; 57:1670-1.

Jansen et al., "Experimental Off-Pump Grafting of a Circumflex Brach via Sternotomy Using a Suction Device", Ann Thorac Surg 1997; 63:S93-6.

Jansen et al., "Off-Pump Coronary Bypass Grafting: How to Use the Octopus Tissue Stabilizer," Ann Thorac Surg. 1998; 66:576-9.

Japanese Journal of Thoracic Surgery, vol. 42, No. 2, 1989.

Kolessov, V.I., M.D., "Mammary Artery-Coronary Artery Anastomosis as Method of Treatment for Angina Pectoris," Thoracic and Cardiovascular Surgery, vol. 54, No. 4, Oct. 1967, pp. 535-544.

Kazama, S. et al., "Fabric Heart Retractor for Coronary Artery Bypass Operations," The Annals of Thoracic Surgery, 55:1582-3, 1993.

Kresh, J. Y., et al., "Heart-Mechanical Assist Device Interaction," Trans. Am. Soc. Artif. Intern. Organs, vol. XXXII, 1986, pp. 437-443.

Lavergne, et al., "Transcatheter Radiofrequency Ablation of Atrial Tissue Using a Suction Catheter," PACE, vol. 12, Jan. 1989, Part II, pp. 177-186.

Lonn, U., M.D., et al., "Coronary Artery Operation Supported by the Hemopump: An Experimental Study on Pigs," The Annals of Thoracic Surgery, vol. 58, No. 1, Jul. 1994, pp. 516-523.

Matsuura, A., et al., "A New Device for Exposing the Circumflex Coronary Artery," The Annals of Thoracic Surgery, 59:1249-50, 1995, pp. 1249-1250.

McGee, M. G.,et al., "Extended Clinical Support with an Implantable Left Ventricular Assist Device," Trans. Am. Soc. Artif. Intern. Organs, vol. XXXV, 1989, pp. 614-616.

McKeown, P.P. et al., "A Modified Sternal Retractor for Exposure of the Internal Mammary Artery," Ann. Thorac. Surg. 32 (1981) 619.

Ochsner, J. L., et al., "Surgical Management of Diseased Intracavitary Coronary Arteries," The Annals of Thoracic Surgery, vol. 38, No. 4, July, pp. 356-362, Oct. 1984.

Parsonnet, V. MD, et al., "Graduated probes for Coronary Bypass Surgery," The Journal of Thoracic and Cardiovascular Surgery, vol. 68, No. 3, 424-26 (Sep. 1974).

Pfister, A. J. M.D., et al., "Coronary Artery Bypass Without Cardiopulmonary Bypass," The Annals of Thoracic Surgery, vol. 54, No. 6, Dec. 1992, pp. 1085-1092.

Phillips, Steven J., M.D. et al., "A Versatile Retractor for Use in Harvesting the Internal Mammary Artery and Performing Standard Cardiac Operations," J. Thorac. Cardiovasc. Surg. (1989; 97:633-5).

Pittman, John, M.D., et al., "Improved Visualization of the Internal Mammary Artery with a New Retractor System," Ann. Thorac. Surg., 1989; 48:869-70.

Riahi, M.,et al., "A Simple Technique and Device to Provide a Bloodless Operative Field in Coronary Artery Surgery Without Cross-Clamping the Aorta," The Journal of Thoracic and Cardiovascular Surgery, vol. 66, No. 6, Dec. 1973, pp. 974-978.

Robicsek, F., "Aortic Spoon-Jaw Clamp for Aorto-Saphenous Vein Anastomosis," J. Card. Surg., 1995; 10:583-585.

Robinson, M. C., et al., "A Minimally Invasive Surgical Method for Coronary Revascularization—Preliminary Experience in Five Patients," Circulation, Oct. 15, 1995, vol. 92, No. 8, 1-176.

Rousou, J. et al., "Cardiac Retractor for Coronary Bypass Operations," Ann Thorac. Surg, 1991; 52:877-8.

Roux, D., M.D. et al., "Internal Mammary Artery Dissection: A Three Dimensional Sternal Retractor," J. Cardiovasc. Surg., 1989; 30:996-7.

Roux, D., M.D. et al., "New Helper Instrument in Cardiac Surgery," Ann. Thorac. Surg., 1989, 48:595-596.

Ruzevich, S. A., et al., "Long-Term Follow-Up of Survivors of Postcardiotomy Circulatory Support," Trans. Am. Soc. Artif. Intern. Organs, vol. XXXIV, 1988, pp. 116-124.

Scholz, K. H., et al., "Transfemoral Placement of the Left Ventricular Assist Device 'Hemopump' During Mechanical Resuscitation," Thoracic and Cardiovascular Surgeon, vol. 38 (1990) pp. 69-72.

Splittgerber et al., "Exposing the Circumflex Coronary Artery: The Heartflip Technique," Ann Thorac Surg. 1996;61:1019-20.

Takahashi et al., "A New Instrument for Immobilization and Hemostasis During Minimally Invasive Direct Coronary Artery Bypass ('MIDCAB doughnut'): Experimental Study", J Card Surg 1997; 12:185-189.

Trapp, et al., "Placement of Coronary Artery Bypass Graft without Pump Oxygenator," Journal of the Society of Thoracic Surgeons and The Southern Thoracic Surgeons Assn. vol. 19, No. 1, Jan. 1975.

Trapp W.G., "To Use or Not To Use the Pump Oxygenator in Coronary Bypass Operations," The Annals of Thoracic Surgery, vol. 19, No. 1, Jan. 1975, pp. 108-109.

Vincent, J.G., "A Compact Single Post Internal Mammary Artery Dissection Retractor," Eur. J. Cardio-Thor. Surg. 3 (1989) 276-277.

Westaby, S., "Coronary Surgery Without Cardiopulmonary Bypass," British Heart Journal vol. 73 pp. 203-205, 1995.

Westaby, S. et al., "Less Invasive Coronary Surgery: Consensus From the Oxford Meeting," The Annals of Thoracic Surgery, 62:924-31, 1996.

Zumbro, G. L. et al., "A Prospective Evaluation of the Pulsatile Assist Device," The Annals of Thoracic Surgery, vol. 28, No. 2, Aug. 1979, pp. 269-273.

English Abstract for Russian Patent No. SU 938967.

* cited by examiner

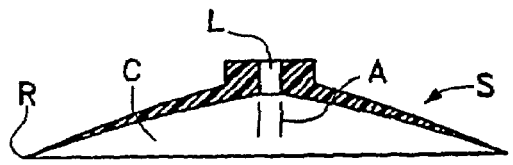
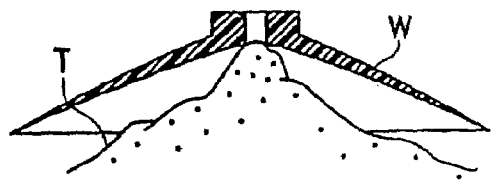
FIG. 6A (PRIOR ART)
FIG. 6B (PRIOR ART)
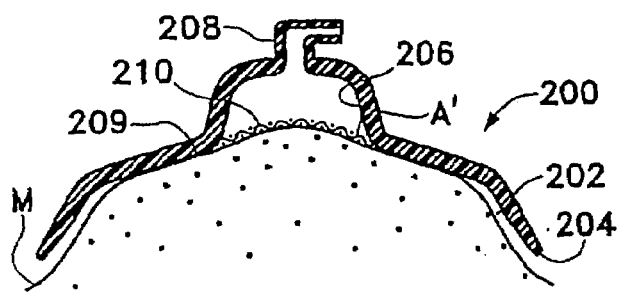
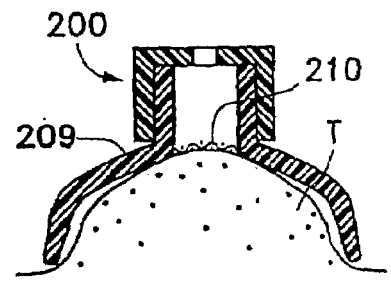
FIG. 7A
FIG. 7B
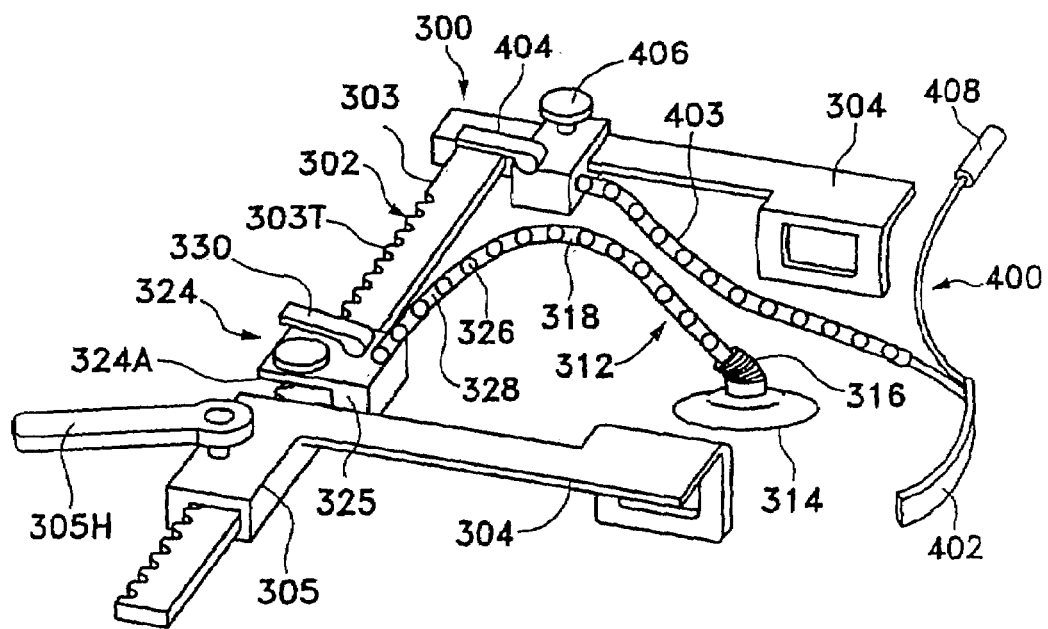
FIG. 8

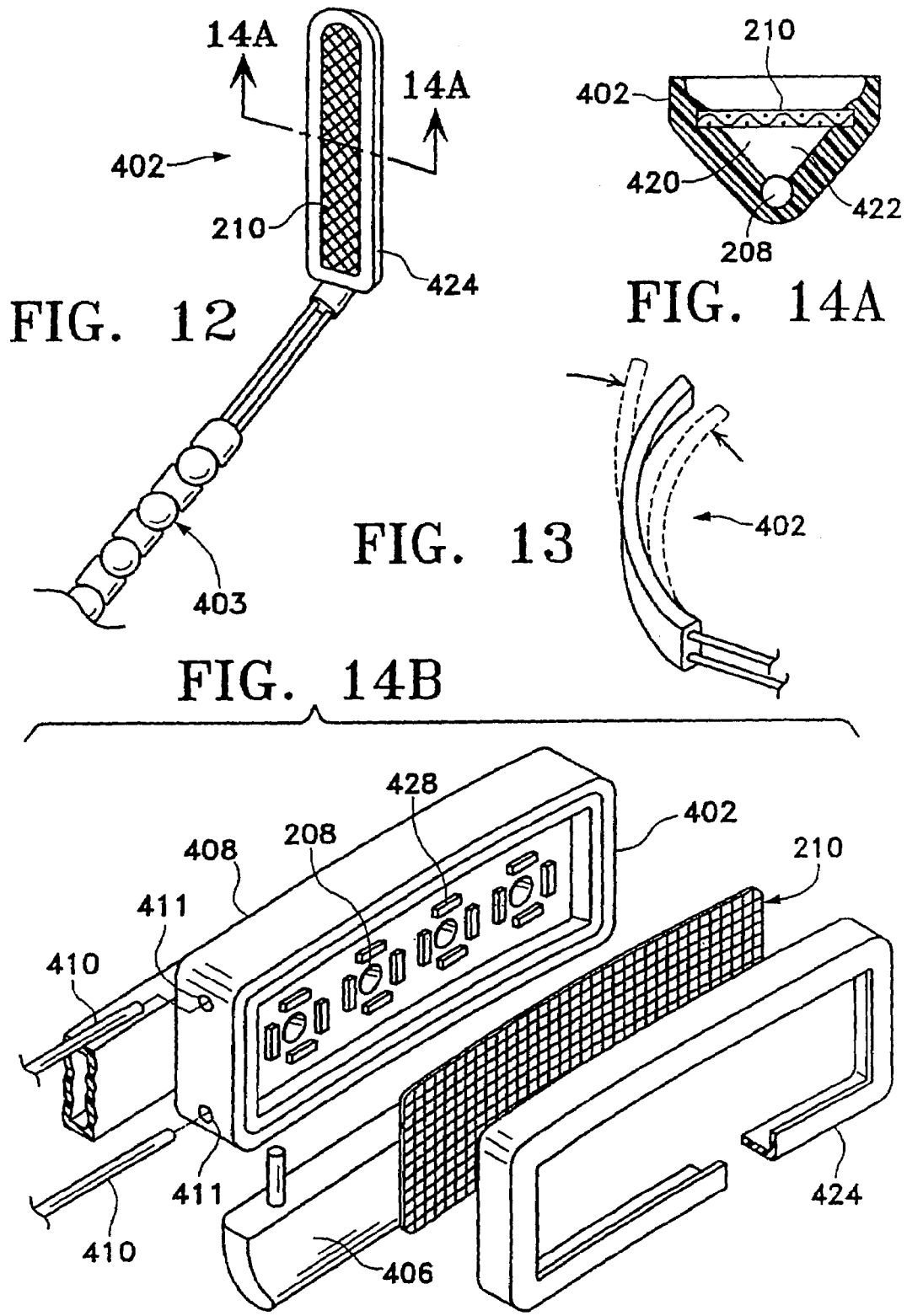

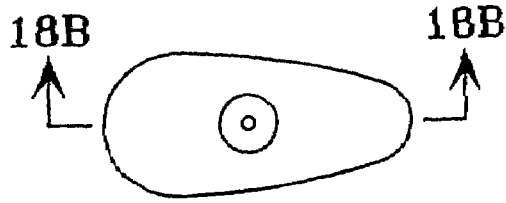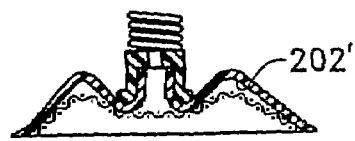
FIG. 18A  FIG. 18B
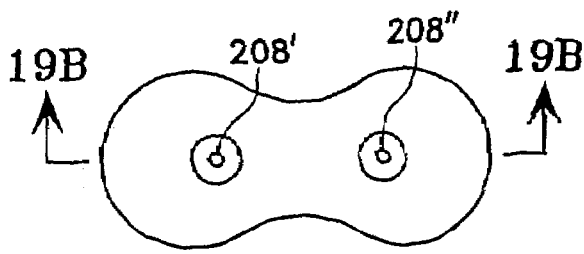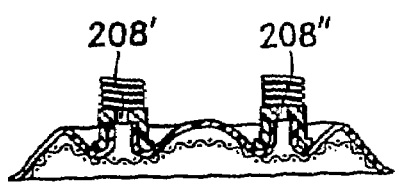
FIG. 19A  FIG. 19B
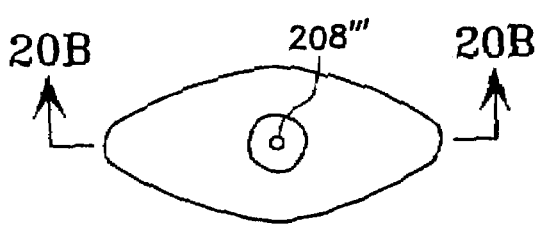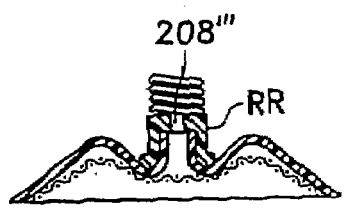
FIG. 20A  FIG. 20B
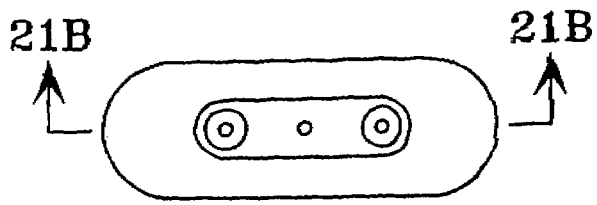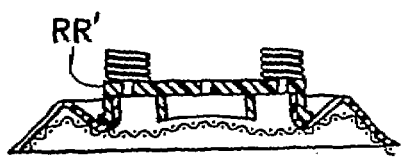
FIG. 21A  FIG. 21B
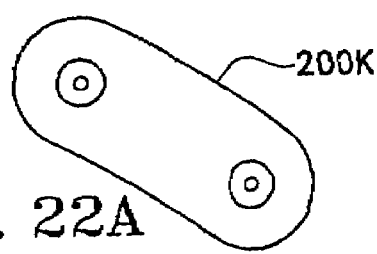
FIG. 22A  FIG. 22B

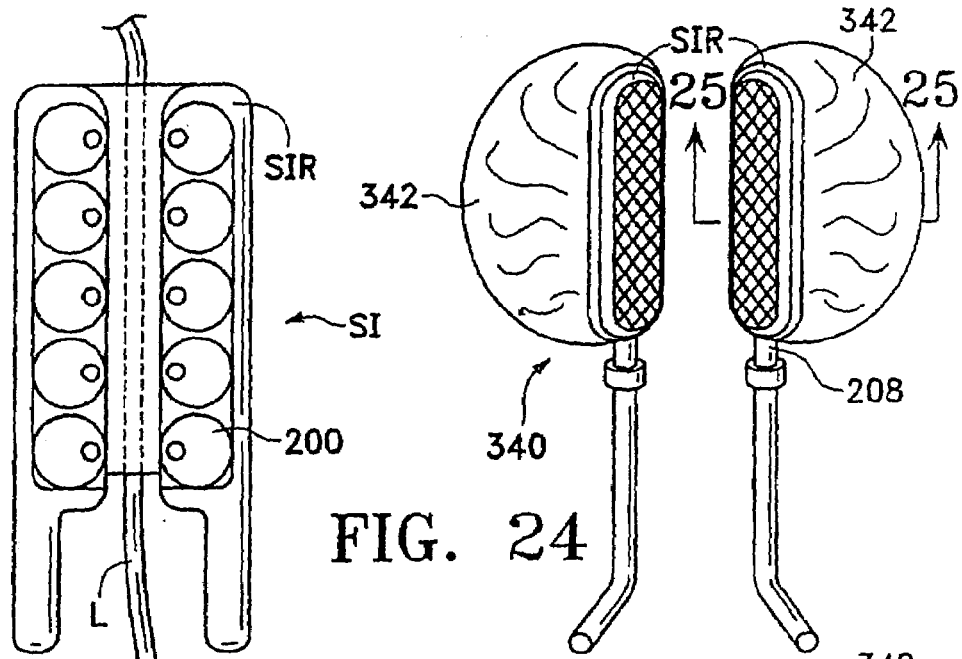
FIG. 23 (PRIOR ART)
FIG. 24
FIG. 25
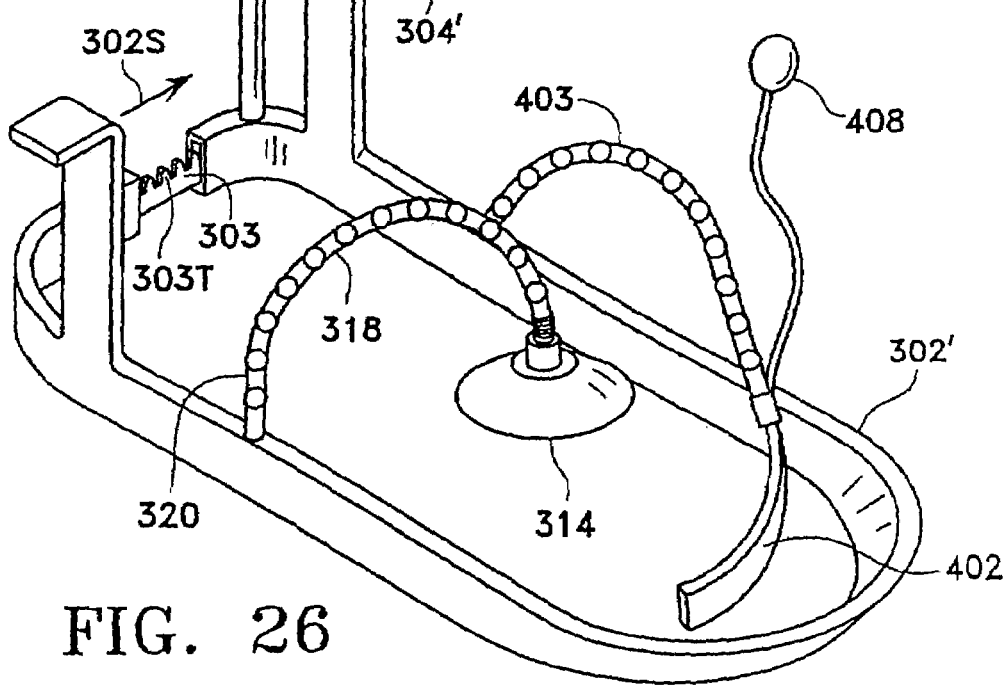
FIG. 26

DEVICE TO PERMIT OFFPUMP BEATING HEART CORONARY BYPASS SURGERY

CROSS REFERENCE TO RELATED APPLICATIONS

This application is a continuation of U.S. application Ser. No. 10/698,798 filed Oct. 31, 2003, now U.S. Pat. No. 7,377,895, which is continuation of U.S. application Ser. No. 09/956,418 filed Sep. 18, 2001, now U.S. Pat. No. 6,743,170, which is a continuation of U.S. application Ser. No. 09/087,511 filed May 29, 1998, now U.S. Pat. No. 6,338,712, which is a continuation-in-part application of application Ser. No. 08/936,184 filed on Sep. 17, 1997, now U.S. Pat. No. 6,019,722. U.S. application Ser. Nos. 10/698,798; 09/956,418; 09/087,511 and 08/936,184 and U.S. Pat. Nos. 6,743,170; 6,338,712 and 6,019,722 are hereby incorporated by reference thereto, in their entireties.

The present application is a continuation-in-part application of co-pending patent application Ser. No. 08/936,184 filed on Sep. 17, 1997 by the inventors of the present application. The disclosure of the just-referenced patent application is incorporated herein by reference.

TECHNICAL FIELD OF THE INVENTION

The present invention relates to the general art of cardiac surgery, and to the particular field of heart retractors used in beating heart surgery.

BACKGROUND OF THE INVENTION

There are as many as 300,000 coronary bypass graft procedures performed annually in the United States. Each of those procedures may include one or more graft vessels. Currently, each graft vessel must be hand sutured. As many as four or more grafts are placed in a procedure. Until recently, coronary artery bypass procedures have been performed with the patient on cardiopulmonary bypass whereby the heart is stopped with cardioplegia and the surgery performed on an exposed and still heart.

Some pioneering surgeons are performing procedures in which the coronary bypass is performed on a beating heart. That is, without heart-lung bypass and cardioplegia. This minimizes the time it takes to perform the procedure and reduces the cost of the operation by eliminating the heart-lung bypass machine.

Coronary Artery Bypass Grafting (CABG) is performed and a new blood supply to the heart muscle is established when coronary arteries are blocked with calcium or plaque. A new blood supply conduit is joined to the diseased coronary, distal to the blockage, thus providing a fresh supply of oxygenated blood to the vessel in question. Today, this is accomplished by hand suturing a graft vessel (the new supply of blood) to the diseased vessel. This junction is called an anastomosis of vessels. Many different types of supply conduits can be used. Examples are cadaver vein, saphenous vein, radial artery, internal mammary artery, and the like.

By way of background, the basic operation of a heart will be briefly discussed. The heart works like a pump. The left and right ventricles are separate but share a common wall (the septum). The left ventricle is thicker and pumps the blood into the systemic circulation. The work it performs is much greater than the right ventricle. The right ventricle pumps blood into the pulmonary circulation, which is a low pressure circuit. The left ventricle wall (a low energy system) is much thinner than the right ventricle.

The left ventricle fills in diastole and ejects in systole. The difference between the diastolic volume (largest) and the systolic volume (smallest) (the stroke volume or amount of blood ejected on each heartbeat) multiplied by heart rate determines the cardiac output of the heart (liters/min. of flow). The heart shortens during systole as the muscle contracts. There are a number of motions during contraction (including a considerable amount of rotation) but for practical purposes the heart can be thought of as a truncated cone. Shortening occurs along its length and also along its diameter. For purposes of this disclosure, the more important of the two motions is the shortening along the diameter since the ejection volume varies as the square vs. along the length which varies with the first power.

The heart functions well whether the person is upright, upside down, prone or supine. It sits inside the pericardium—a sac which limits its motion and spreads the support on the heart so that no matter how a person positions himself, it is not particularly compressed and is able to fill and then eject with each heartbeat. The concept of the pericardium spreading the load is critical, i.e., when lying supine, the posterior pericardium supports the heart over a large surface of the heart just as when the person is lying on his stomach, the front of the pericardium spreads the load.

When the chest is opened by a median sternotomy it is possible to gain access to all chambers and surfaces of the heart. This combined with the fact that this incision is usually less painful than a thoracotomy (rib separation), makes this the preferred surgical approach to the heart.

The coronary vessels are surface vessels, only occasionally dipping into the myocardium making them accessible without opening the heart. Traditionally, bypass surgery is done with the heart arrested. This stops the motion of the heart and allows the arrest of the coronary circulation so the surgeon sews in a bloodless and easy to see field. Since the heart is stopped, the patient would suffer irreversible damage to the brain and other tissues and organs without the use of the heart-lung machine to support the general circulation. Although the heart-lung machine has been refined, it is particularly toxic to older and debilitated patients and it is expensive.

It is possible to perform surgery off bypass, while the heart is beating and the coronaries are under positive blood pressure; however, there may be problems. One problem is that not all vessels are accessible since some vessels are on the posterior or inferior surfaces and that when such vessels are brought into view by lifting the heart, cardiac performance is impaired such that the cardiac output falls and blood pressure drops. A second problem is that the heart moves so that suturing in vessels (12 to 15 stitches in a vessel under 2 mm in diameter) might be inaccurate and a third problem is that there is blood in the field as the coronary circulation is not interrupted. This last problem is now largely solved by snares, which temporarily stop the flow of blood through the targeted arteries. The problem of lifting the heart is not to impair the performance of the heart while at the same time adequately exposing the heart and regionally immobilizing the vessel during beating heart surgery, and this problem is not solved with any prior art system.

For the heart to be effective, it must have adequate biventricular function (both right and left ventricles). The left ventricle pumps into the high resistance systemic circulation and is thicker and generates considerably more energy than the right ventricle. It is primarily circular in cross section. This displacement of blood (and thus heart output) depends on shortening in the short axis (diameter of the cross section) and to a lesser degree on shortening in the long axis (apex to base).

There is also rotational motion to the heart as it contracts, thus imparting multiplanar motion to the heart as it beats; still further, the surface of the heart undergoes multiplanar movement during operation of the heart. The right ventricle pumps into the lower resistance pulmonary circulation and is much thinner and its energy generation is much less than that of the left ventricle. Function of both of these ventricles must be maintained during surgical manipulation of a beating heart.

Therefore there is a significant need for a means and a method for moving a beating heart so as not to impair the performance of the heart while at the same time adequately exposing the heart and regionally immobilizing a vessel during beating heart surgery.

Lifting of the heart is deleterious to heart function for several reasons. First, the lifting of the heart impairs the venous return to the heart so that there is less diastolic filling of the heart (this can largely be corrected by putting the head down and the feet up to increase venous return). Second, the heart is distorted. Using a hand or spatula to lift the heart is quite different than simply changing body position when the heart is inside the chest. The force applied by the hand to the heart is localized so that the heart is no longer a truncated cone, but is much flatter. This shape is much less effective for ejection (the circle is the most effective as it has the highest ratio of volume to diameter) and flattening also limits the diastolic volume so that inadequate filling occurs. Third, lifting pressure applied to a beating heart may deleteriously affect valve function of the heart, in particular, the mitral valve function may be adversely affected by such lifting.

In order to perform cardiac surgery on a beating heart, there is a need to lift, support and orient the heart without reducing its ability to function. Therefore, there is a need for a means and method to move and orient a beating heart into position so any vessel of the heart can be accessed without unduly interfering with the operation of the heart, especially the mitral valve function.

In coronary bypass operations, grafts have to be anastomosed to the anterior descending artery (right coronary artery branch), the circumflex artery, and to the posterior descending artery. The anterior descending artery lies on the front surface of the heart and is easily accessible to the surgeon without particular help from surgical assistants or using any devices. The circumflex and posterior descending arteries, however, lie on the back surface of the heart. Therefore, to expose the circumflex artery to a field of view of the surgeon, it is mandatory to lift the heart and rotate it about the axis of the inferior vena cava and the superior vena cava. Likewise, to expose the posterior descending artery, it is necessary to lift the heart and rotate it in the direction of its apex. If the heart is moved improperly, it may go into fibrillation.

Ordinarily, a surgical assistant is employed to lift the heart by using his or her hand, this is satisfactory for an arrested heart. However this is not satisfactory for a beating heart. However, it is very difficult and tiring to keep the heart in a steady position. Furthermore, the myocardium in contact with the assistant's fingers may be damaged by pressure, avulsion, and premature rewarming. Further, the assistant's hand in the operative field can get in the way, and the assistant, who often stands next to the surgeon may restrict the surgeon's movements.

To date, with the exception of the device disclosed in the parent application, devices that have been directed toward facilitating beating heart surgery have been very simple stabilization platforms. A two-tined fork is the simplest and works well on directly exposed vessels such as the LAD. Another device is comprised of a hollow support tube which can be clamped outside the patient's body cavity. The support tube terminates in a suction head with a number of suction ports arranged in a linear row in such a way that they resemble the suction cups of an octopus. These suction heads are attached to the myocardium and ideally allow the heart to be regionally immobilized on either side of the target artery. This allows for a very localized stabilization of an artery to perform an anastomosis. This tool accomplishes the requirements for immobilizing the target artery for surgery. However, this tool is inadequate for actually lifting the heart to gain access to vessels located on the posterior and lateral surfaces (circumflex and right coronary distributions). This device really is a local stabilizer, and cannot be adequately employed to assist in the lifting or moving of the heart, which is necessary in some instances, such as for a large heart, or the like. However, it has also acquired another role, that of vessel presentation. Unfortunately, the device was not implicitly designed for this function. Vessel presentation during beating heart surgery is a different function and more complex since it must allow the entire heart to function. Yet it is the more commercially valuable application of this tool since there are no other mechanical stabilizers available which are simple and acceptable to lift the functioning heart to access all vessels and eliminate the need for cardio-pulmonary bypass.

Therefore, there is a need to provide a tool that is commercially viable and which can be used for vessel presentation, and which can be used to assist in lifting and/or orienting the heart when needed.

The surgeon would like a very localized, immobilized area, such as one to two cm, on either side of the target vessel. The above-mentioned tool immobilizes the heart transmurally for a distance of two to 3 cm on each side. Small suction heads, like the surgeon prefers for local immobilization, unfortunately cannot lift the heart and larger suction heads impair heart function by immobilizing too large an area around the suction head. If several rigid heads are used circumferentially around the heart in order to lift it, a large amount of the heart is prevented from contraction. This will immobilize too much of the heart circumference to maintain effective heart function.

Therefore, there is need for a means and method for immobilizing a particular area on the heart without unduly interfering with the functioning of the heart, and which can be used to lift the heart as well, again, without interfering with the operation of the heart. There is also a need for a system for manipulating a heart during cardiac surgery which will support the heart in position for coronary bypass surgery of the circumflex coronary artery and posterior descending artery.

Still further, the myocardium of a beating heart undergoes multiplanar movement and motion during operation of the heart. A suction cup applied to such a moving surface may have a tendency to become separated from the myocardium thereby interrupting the suction being applied to the heart. Such interruption of suction may interfere with the attachment of the device to the heart.

Therefore, there is a need for a means and method for manipulation of a heart during cardiac surgery that will not be impaired by movement of the myocardium during operation of the heart.

One remedy for this problem is to make the suction cups larger. However, this is not practical since too much of the myocardium might be influenced by such a solution.

Therefore, there is a need for a means and method for manipulation of a heart during cardiac surgery that will not be impaired by movement of the myocardium during operation of the heart, while influencing a minimum amount of the myocardium.

Another prior art method of supporting a heart is by use of a sling. A sling is a network of fabric or plastic that is placed around the heart in the manner of a hammock. The heart is then supported by the sling. It is noted that in order for a sling to work as a retractor, the surgeon is required to arrange the ties to be pulled from the proper direction, such as normal to the desired direction of lift, which can be onerous. This presents a serious problem since there are no easy reference points above the patient in which to attach these ties.

While the art has included several inventions intended to support the heart during coronary bypass surgery of the circumflex coronary artery, these inventions have several drawbacks that have hindered their acceptance in the art. For example, the use of nets to support the heart exposes the heart to fine strands which impinge on the heart and may cause damage. Furthermore, nets may impede the surgical target and require special techniques or procedures to remove the net from the surgical target area. This is especially onerous if the net mesh is fined. Flat cloth tapes are a form of net, and may damage the heart due to a rough texture of the cloth and the small area of contact between the tape strands and the heart. Further, tapes and similar devices that do no have large surface areas contacting the heart may not support the heart in a uniform manner and may create large pressure areas at the contact points.

Therefore, there is a need for a manipulation system for use in cardiac surgery which will support the heart in position for coronary bypass surgery of the circumflex coronary artery in a manner that will not damage the heart yet will provide easy access to the surgical target and keeps working while cardiac output is maintained.

Still further, some prior art means for supporting the heart during cardiac surgery may tend to interfere with ventricle operation.

Therefore, there is a need for a means and a method for manipulating a heart during cardiac surgery which will not interfere with ventricle operation of the heart while a beating heart is supported in position and orientation for surgery.

The parent disclosure discussed a means and method for lifting the heart during surgery. This means and method included a gross support means for engaging the apex portion of the heart and which is fixed to a stationary element, such as the operating table or the like. The preferred form of the gross support means includes a cup-shaped element that fits around the apex of the heart to support the weight of the heart and which is attached to a source of suction.

The means and method disclosed in the parent disclosure work well, but the inventors have since discovered that it would be beneficial to the overall success of beating heart surgery to contact the least amount of myocardium as possible in moving the heart for surgery.

A further consideration in coronary artery surgery is hemorrhage from the incision into the coronary artery at the proposed anastomotic site. Therefore, heretofore, coronary artery surgery has been carried out under conditions of cardiac arrest and aortic root cross clamping. Hence, the myocardium is temporarily deprived of coronary blood supply. In some patients, an additional coronary blood supply, through the form of bronchial circulation, causes significant hemorrhage during the bypass grafting process. This hemorrhage is inconvenient, as it masks the surgeon's view during the delicate suturing process, and threatens the well-being of the patient. Performing surgery in this manner has several additional drawbacks, including the need to stop the heart, the need to insert special equipment and procedural steps to carry out the function of moving blood through the patient's body while the heart is stopped.

Therefore, there is a need for a heart retractor which will support the heart in position for coronary bypass surgery of all of the coronary arteries, including the circumflex coronary artery, in a manner such that the tool does not damage the heart while cardiac output is maintained yet will provide easy access to the surgical target and which can be used in a manner that does not require the heart to be stopped.

Still further, there is a need for a system for manipulating the heart during cardiac surgery which permits regional as well as specific immobilization of the heart.

However, the continued operation of the heart will produce problems, in addition to the above-discussed problems, of forming a moving target for the surgeon. That is, since the heart continues to beat during the operation, the surgical target will move in connection with such beating movement. The heart cannot be stopped or unduly constrained without increasing the danger of fibrillation.

Therefore, there is a need for a system for manipulating the heart during cardiac surgery which will support a beating heart in position for coronary bypass surgery of coronary arteries in a manner that will not damage the heart yet will provide specific and regional support while allowing unabated cardiac output.

Recently, there has been interest in minimally invasive coronary bypass surgery. This is not surprising since a median sternotomy and a run on the cardiopulmonary bypass pump are not well tolerated by some patients, combined with the added cost of coronary bypass equipment and staff. The procedure results in considerable recovery time and is associated with a risk of death and major complication. While the ultimate goal is to provide bypass to all vessels by port access (like gallbladder surgery) and to eliminate the need for cardiopulmonary bypass, a more limited but reasonable option for the next number or years will be to perform bypass off pump with an incision (sternotomy or thoracotomy). A tool which could allow performance of multivessel off pump bypass would be most helpful.

Therefore, there is a need for a heart retractor which will support the heart in position for minimally invasive coronary bypass surgery of coronary arteries, including the circumflex coronary artery, in a manner that will not damage the heart yet will provide easy access to the surgical target without requiring the heart to be stopped yet without unduly constraining the heart.

Still further, the inventors have observed that not all hearts are the same size, shape and have the same spacing between corresponding areas. Thus, while all hearts are basically the same, there may be a variation between individual hearts. Therefore, a device that supports a heart should account for these variations. This is especially true if the heart is to continue pumping during the operation and while it is supported. If the support is not fit to the particular heart, it may constrict the heart in some manner and thus interfere with the continued output of the heart.

Therefore, there is a need for a system for manipulating a heart during cardiac surgery which will support a heart, especially a beating heart, during cardiac surgery and which can be adjusted to fit the particular needs of the individual heart and will support the heart both in gross and regionally.

OBJECTS OF THE INVENTION

It is main object of the present invention to provide a system for manipulating a heart during cardiac surgery which will support the weight of a beating heart and maintain cardiac output unabated and uninterrupted even though the heart is maintained in an unnatural position and/or orientation.

It is another object of the present invention to improve the retractor disclosed in the parent disclosure.

It is a further object of the present invention to provide a system for manipulating a heart during cardiac surgery which will support a beating heart in position for coronary bypass surgery and which can support the heart both regionally and in gross.

It is a further object of the present invention to provide a system for manipulating a heart during cardiac surgery which will support a beating heart in position for coronary bypass surgery and which can support the heart both regionally and in gross and which can account for variations in individual hearts.

It is a further object of the present invention to provide a system for manipulating a heart during cardiac surgery which will support a beating heart in position for coronary bypass surgery of the coronary arteries, including the circumflex coronary artery.

It is another object of the present invention to provide a system for manipulating a heart during cardiac surgery which will support the heart in position for coronary bypass surgery of the coronary arteries in a manner that will not damage the heart yet will provide easy access to the surgical target.

It is another object of the present invention to provide a system for manipulating a heart during cardiac surgery which will support the heart in position for coronary bypass surgery in a manner that will not damage the heart yet will provide easy access to the surgical target and which can be used in a manner that does not require the heart to be stopped.

It is another object of the present invention to provide a system for manipulating a heart during cardiac surgery which can support the heart while maintaining competent mitral valve function.

It is another object of the present invention to provide a system for manipulating a heart during cardiac surgery which will support the heart in position for coronary bypass surgery in a manner that prevents collapse of the right ventricle during manipulation of the heart.

It is another object of the present invention to provide a system for manipulating a heart during cardiac surgery which will support the heart in position for coronary bypass surgery in a manner that will not damage the heart yet will provide easy access to the surgical target without requiring the heart to be stopped yet without unduly constraining the heart.

It is another object of the present invention to provide a system for manipulating a heart during cardiac surgery which will support the heart in position for minimally invasive coronary bypass surgery in a manner that will not damage the heart yet will provide easy access to the surgical target without requiring the heart to be stopped yet without unduly constraining the heart.

It is another object of the present invention to provide a system for manipulating a heart during cardiac surgery which will provide regional and specific immobilization of the heart.

It is another object of the present invention to provide a system for manipulating a heart during cardiac surgery which will isolate one region of the heart while allowing cardiac output to be sustained.

SUMMARY OF THE INVENTION

These, and other, objects are achieved by a system for manipulating a heart during cardiac surgery which suspends the heart from the apical region near the right ventricle and prevents collapse of the right ventricle during the manipulation. The heart can be supported by this suspension, but also has a gross support that is located near the left ventricle and extends along the arterial ventricular (AV) groove to lift and rotate the heart while supporting the mitral valve annulus to maintain competent valve function of the mitral valve. Two-point support can thus be provided in a manner that maintains cardiac operation unimpeded. Still further, the system can include a surgical target immobilizing means that is, itself, capable of assisting in the lifting of the heart under some circumstances and thus can be used to assist in the movement of the heart during cardiac surgery. The location and design of the elements of the system of the present invention achieves the lifting and orienting of the heart in a manner that presents the heart in the most advantageous position and orientation for surgery while permitting the heart to maintain cardiac output in an essentially unabated manner. This provides a stationary target for the surgeon while supporting the heart in a safe manner and in a manner that does not interfere with the surgeon or his field of sight. In this manner, the system of the present invention can be used to support a heart during cardiac surgery without requiring an assistant to hold the heart, yet will permit the surgical procedure to be carried out without requiring cardiac arrest.

Furthermore, the system of the present invention includes a frame that is located within the patient's thoracic cavity whereby movement of the patient automatically moves the heart supporting elements in a corresponding manner. This maintains the surgical work field clear and automatically repositions and reorients the heart supporting elements as the patient is moved. This efficiently keeps the heart supported during surgery.

More specifically, a first form of the system for manipulating a heart during cardiac surgery includes an element that can be cup-like and which has a flexible rim that engages the myocardium of the heart in a manner that maintains the engagement even while the myocardium moves during heart operation. Still further, the cup-like element is designed so that heart tissue will not interfere with the operation of the element. The cup-like element applies suction to the heart to hold the element associated with the cup-like element on the heart. The cup-like element is used in connection with the suspension head discussed above as well as in connection with the surgery target immobilizing element. Flexible means on the cup-like element permit that element to move to accommodate multiplanar movement of the heart during operation of the heart. Still further, the gross support means may also use suction to hold the support against the heart. If used, the suction interface is designed so heart tissue will not interfere with the suction applied via the gross support means. The design of the suspension head, the suction cups and the surgical target immobilizing means is such that the system of the present invention can accommodate an individual heart and is amenable to use on hearts of different sizes, weights and even locations. In this manner, a heart, especially a beating heart, can be supported in the manner that is most effective for that particular heart. Thus, in the case of a beating heart, cardiac output can be maintained in an unabated and uninterrupted manner as there will be virtually no constrictions on the heart because the support will be perfectly fitted the particular heart.

A form of the system of the present invention can be used in minimally invasive surgery. The system may include a handle on the gross support means to move the gross support means as required, and a handle can be placed on the target-immobilizing means to move that means as necessary as well. The distal ends of the handle are located to provide access to the handle while remaining unobtrusive during surgery. Detachable handles could also be used whereby the handles are removed after correct placement of the head.

While this invention is disclosed in the preferred form for open chest procedures for beating heart surgery, it may also be utilized for minimally invasive procedures as well as those that use cardioplegia due to its novel time saving and enabling features. It is also noted that this disclosure is not directed to the art of anastomosis per se. However, it is directly related to enabling a surgeon to perform an anastomotic procedure in a precise and controlled manner.

The inventive device disclosed herein eliminates the need for use of the heart-lung machine. It allows a surgeon to lift and displace the heart to expose all vessels to regionally immobilize them for suturing without seriously impairing heart performance.

The advances made using the retractor disclosed in the parent disclosure are thus improved.

Once the stabilization of the beating heart has been achieved as with the system of the present invention, it then becomes more feasible to entertain the idea of performing this surgery in a minimally invasive manner precluding the need for the median sternotomy.

BRIEF DESCRIPTION OF THE DRAWING FIGURES

FIGS. 6A and 6B illustrate operation of a prior art suction cup.

FIGS. 7A and 7B illustrate operation of a multipart suction cup embodying the present invention.

FIG. 8 is a perspective view of a system for manipulating a beating heart during cardiac surgery embodying the present invention.

FIG. 12 shows a portion of the gross support means of the retractor of the present invention.

FIG. 13 is a top plan view of the flexible head of the gross support means of the retractor.

FIG. 14A is a view along line 14A-14A of FIG. 13 showing the mesh means that prevents heart tissue from interrupting suction applied to maintain the gross support means in place on the heart.

FIG. 14B is an exploded view of the gross support means shown in FIG. 12.

FIGS. 18A and 18B show another configuration of the flexible suction cup of the present invention.

FIGS. 19A and 19B show another form of the multisection suction cup.

FIGS. 20A and 20B show another form of the multisection suction cup.

FIGS. 21A and 21B show another form of the multisection suction cup.

FIGS. 22A and 22B show another form of the multisection suction cup.

FIG. 23 shows a bottom plan view of a prior art tool used to immobilize a section of a beating heart to define a surgical target.

FIG. 24 is a bottom plan view of a means of the present invention for immobilizing a surgical target area of a beating heart.

FIG. 25 is an elevational view of the means of the present invention for immobilizing a surgical target area.

FIG. 26 is a perspective view of an alternative form of the retractor of the present invention.

DETAILED DESCRIPTION OF THE PREFERRED EMBODIMENT OF THE INVENTION

Figure 1:
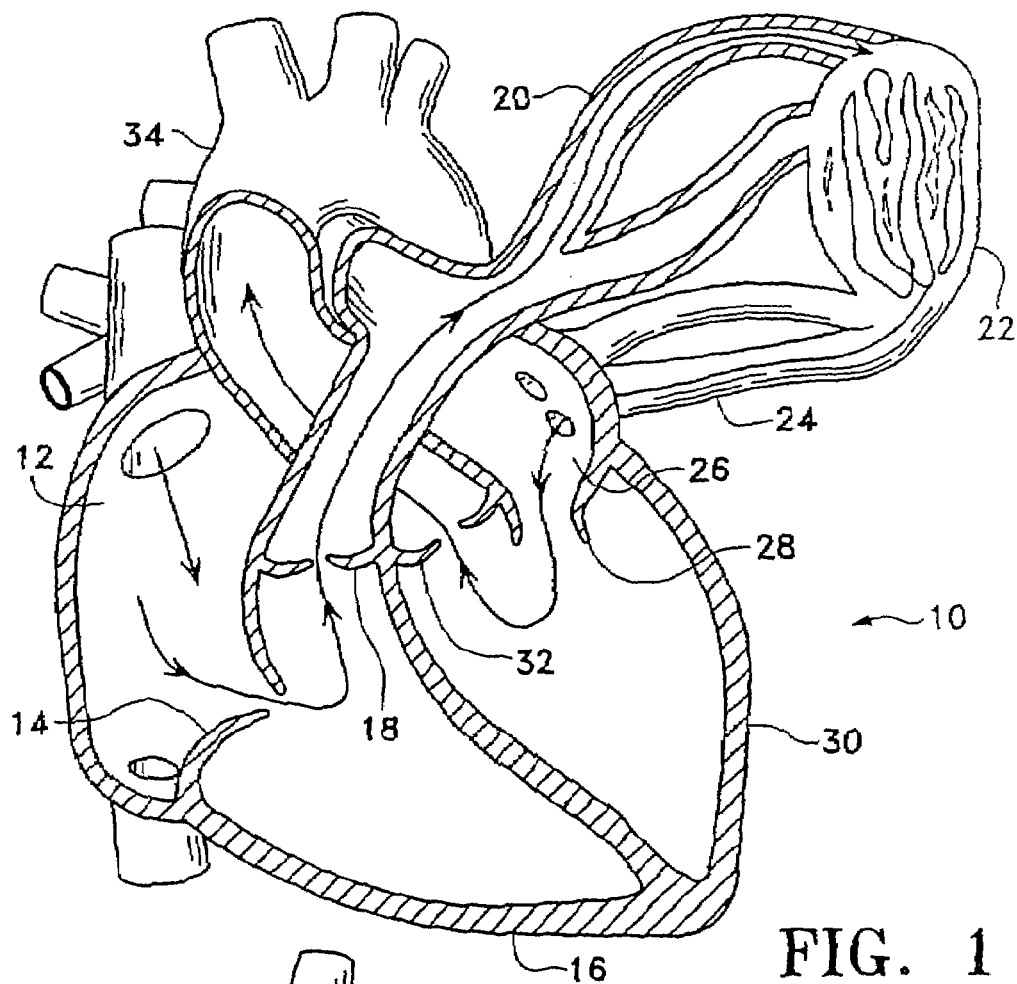
FIG. 1 illustrates blood flow in a normal heart.

By way of introduction, the operation of a heart will be discussed before describing the system embodying the present invention. In FIG. 1, the normal circulatory pattern of blood through heart 10 is illustrated. Blood from the venous system enters the first chamber of the heart, the right atrium (R.A.) 12. From right atrium 12, it passes through tricuspid valve 14 into right ventricle (R.V.) 16 via pulmonic valve 18, entering pulmonary artery 20 which leads to lungs 22. In lungs 22, carbon dioxide is released and the blood is reoxygenated. Blood then exits lungs 22 back into pulmonary vein 24 which leads to left atrium (L.A.) 26. From left atrium 26, blood passes through mitral valve 28 into left ventricle (L.V.) 30. Blood then exits heart 10 via aortic valve 32 into aorta 34 and the generalized arterial circulation.

Cardiac contraction is orchestrated by electrical impulses originating from the heart's nervous system. Electrical stimulation to the myocardial fibers results in muscular contraction. Specifically timed electrical signals originating in the upper chambers of the heart cause the atriae to contract and empty blood into the ventricles 16 and 30. After atrial contraction, a short electrical delay takes place. This pause allows the ventricles 16 and 30 to receive blood from atriae before they are stimulated to contract. With ventricular contraction, blood is ejected from heart 10.

FIGS. 2A-2E illustrate a simplified diagram of normal cardiac contraction as visualized from left ventricle 30. The cardiac cycle can be broken down into two major stages: diastolic and systolic. Diastolic is the relaxation phase of the ventricular contraction cycle. During this time the ventricle relaxes and fills up with blood in preparation for the next contraction. Systole is the ventricular phase involved with contraction and the process of ejecting blood from the heart.

Figure 2A:
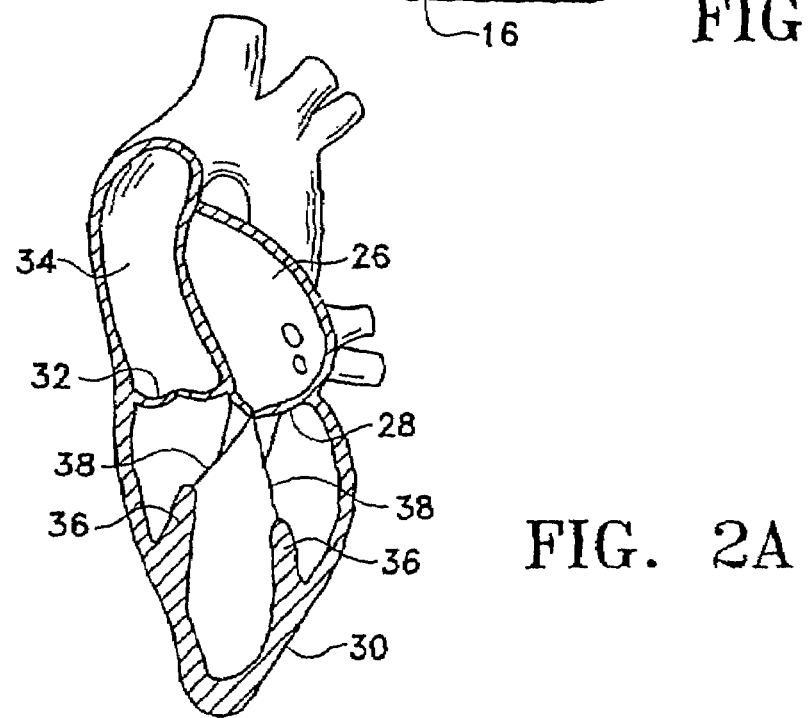
FIGS. 2A-2E illustrate the pumping action of a normal heart.

FIG. 2A illustrates the first phase of diastole which is isovolumetric relaxation immediately following a systolic contraction. This represents the transition phase between diastole and systole.

Figure 2B:
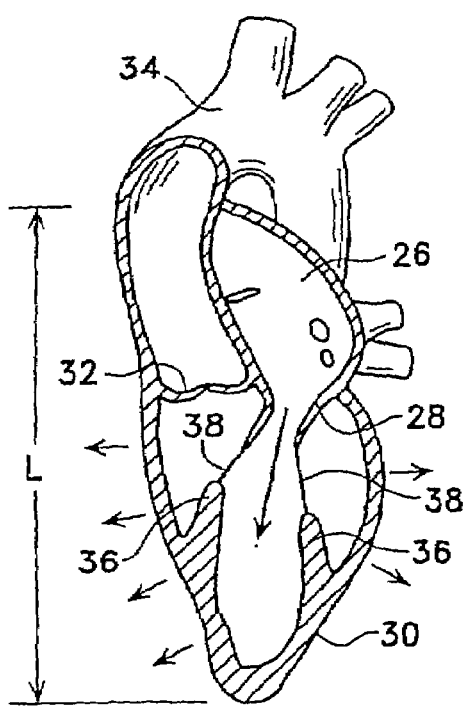

FIG. 2B illustrates that with further ventricular relaxation, a building of negative pressure within the ventricle due to dilation results in a rapid influx of blood. Additionally, the geometric angle formed between the ventricular wall, papillar muscle (P.M.) 36, chordac tendinea (C.T.) 38 and mitral valve (M.V.) 28 widens. This combined process results in the opening of mitral valve 28.

Figure 2C:
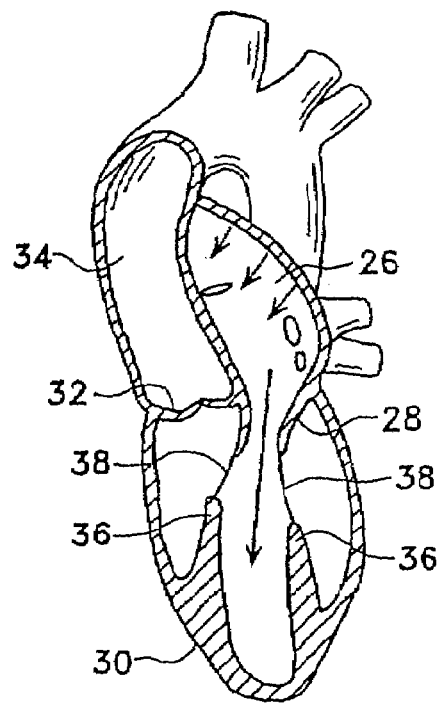

FIG. 2C illustrates the latter stages of diastolic ventricular filling. During this phase, left atrium 26 contracts to allow for maximal ventricular filling.

Figure 2D:
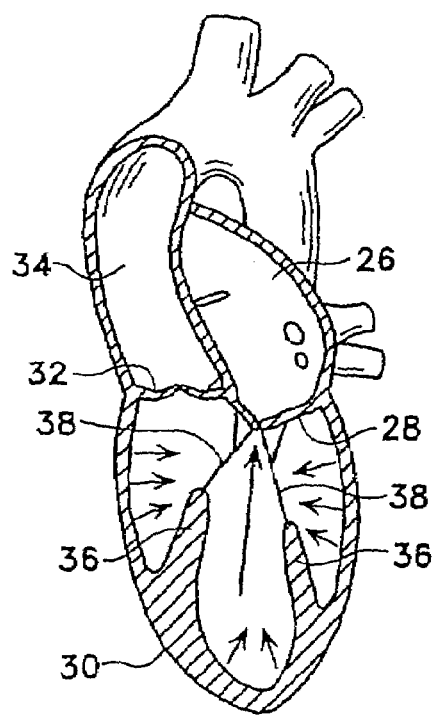

In FIG. 2D, left ventricle 30 begins to build muscular tension prior to actually contracting and secondarily reducing ventricular volume. This phase demonstrates isovolumetric contraction and is referred to as pre-systole. With building ventricular contraction, the intraventricular pressure increases which helps force mitral valve 28 closed. Additionally, the geometric relationship between the valve cusp and muscle-tendon supporting structures narrows with ventricular contraction which assists in mitral valve closure.

Figure 2E:
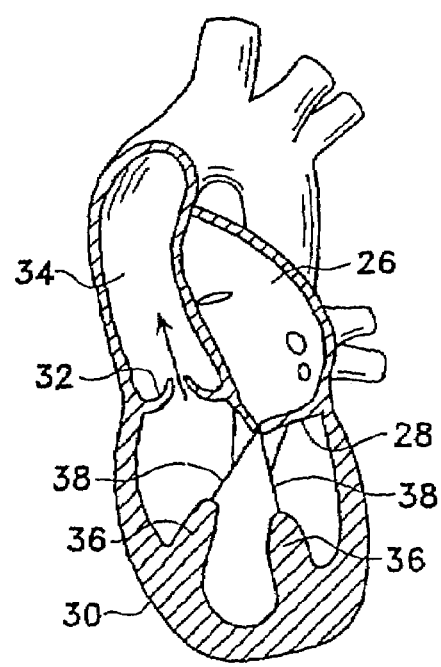

FIG. 2E illustrates that as ventricular contraction progresses, the intraventricular volume decreases and pressure builds. Once the ventricular pressure exceeds the blood pressure within aorta 34, aortic valve (A.V.) 32 is pushed open. Blood is then ejected from the ventricular cavity into aorta 34. This phase is called systole.

By way of further introduction, the retractor disclosed in the parent disclosure will be briefly discussed. The retractor disclosed in the parent disclosure clamped the heart in a manner that restricts the length dimension while permitting the other dimensions to change. By immobilizing the heart in a direction along dimension L, but allowing the remainder of the heart to operate in a normal manner, operation of the heart is not restricted. The retractor of the present invention further immobilizes only the specific surgery target area whereby the remainder of the heart operates in an unrestricted manner. Thus, only the specific surgery location is immobilized. This is all that is required for a successful surgery and the entire heart need not be immobilized. The system for manipulating a heart during cardiac surgery of the present invention also lifts the heart in a manner that permits unrestricted operation of the heart as well.

Figure 3:
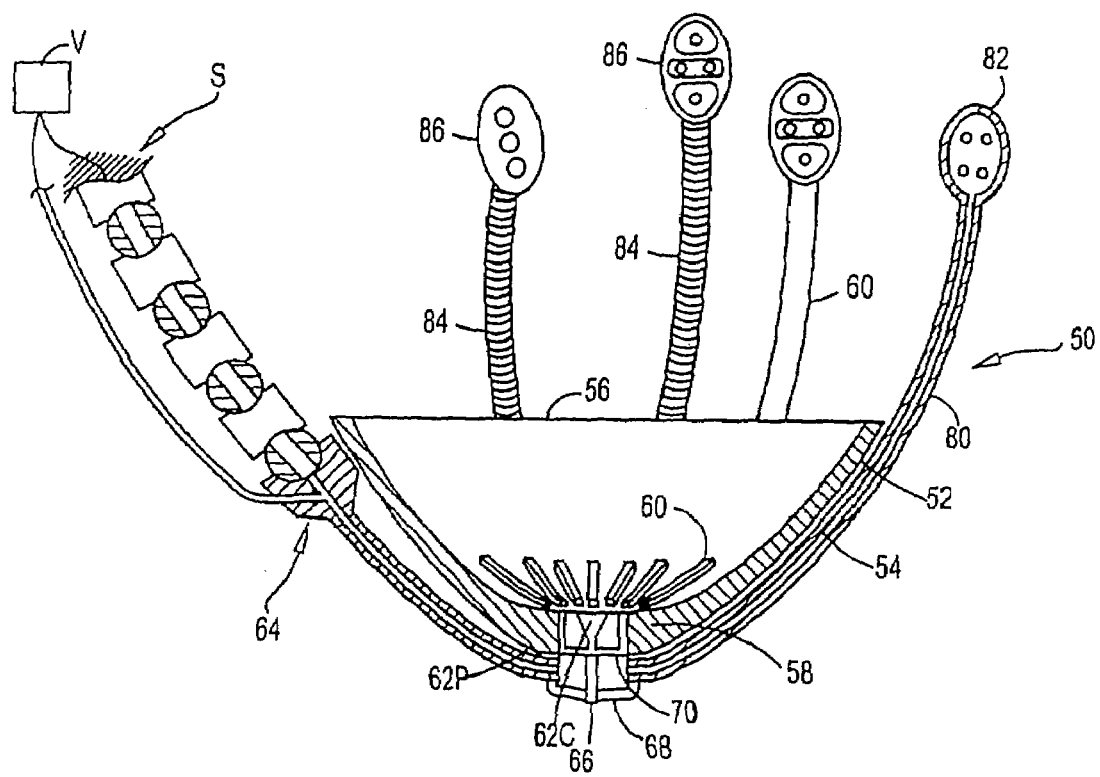
FIG. 3 is a sectional elevational view of the system for manipulating a heart during cardiac surgery disclosed in the parent application.
Figure 4:
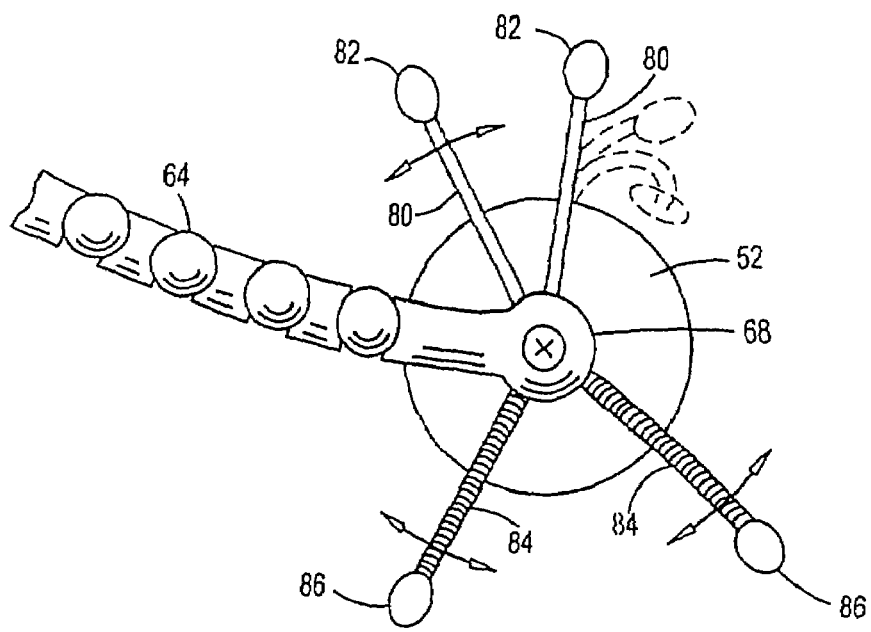
FIG. 4 is a bottom view of the system for manipulating a heart during cardiac surgery disclosed in the parent application.
Figure 5:
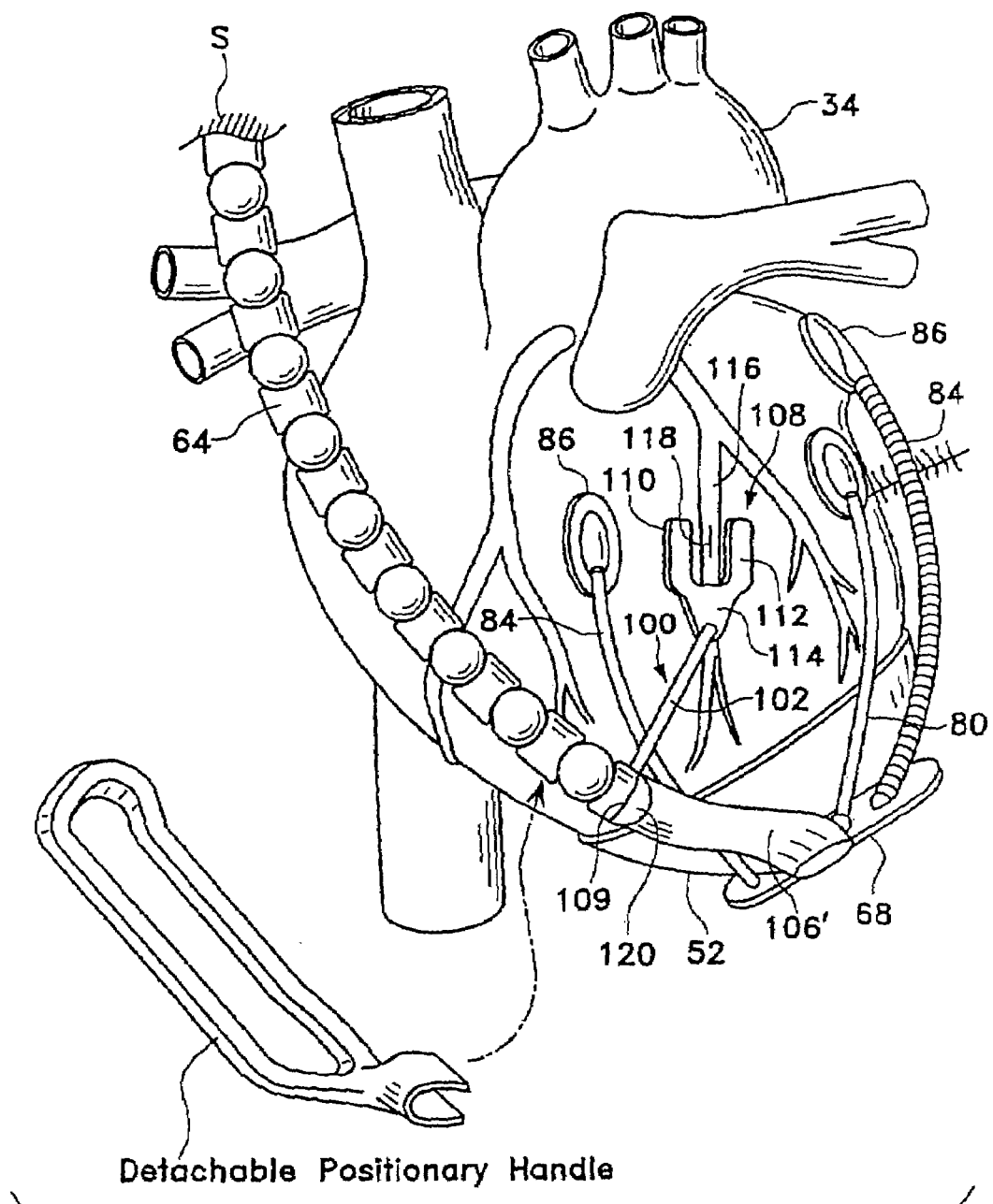
FIG. 5 is a perspective view of the system for manipulating a heart during cardiac surgery of the parent application in place on a heart.

Since the present invention is an improvement over the parent disclosed invention, it will be instructive to briefly review that parent retractor. Further discussion of the parent retractor can be found in the parent disclosure which is incorporated herein by reference. Referring specifically to FIGS. 3-5, system for manipulating a heart during cardiac surgery 50 of the parent invention is shown in detail. The retractor permits regional and specific immobilization of the heart while permitting essentially unabated cardiac output whereby all coronary arteries, including the circumflex coronary artery, to be bypassed and the heart maintained in an unnatural position and/or orientation. The retractor includes a gross support means 52 for engaging an apex portion (gross weight) of a heart to support the heart when the heart is lifted for surgery. Support means 52 includes a cup-shaped portion 54 having a top rim 56 and an apex 58 with ribs 60 defined adjacent to the apex to support the heart in the cup-shaped element. While a cup-shaped element is preferred, one could substitute other attachment configurations without departing from the scope of this disclosure. The only requirement is that the element be sized and shaped to adequately support the heart to achieve the results discussed herein, to wit: supporting the heart in an orientation suitable for the type of heart surgery of interest here. Thus, no limitation as to specific shape is intended for element 52. Vacuum ports 62c and 62p are defined through the cup-shaped element at apex 58 to be fluidically connected with a vacuum source for securing the heart in place in the cup-shaped element. A vacuum source V is fluidically connected to holes 62c and 62p via main support arm 64 which has one end thereof fixed to a stationary support S (see FIG. 5), such as the operating table, or a rib spreader, and the other end thereof attached to the cup-shaped element via fastener 66 attached to anchor 68. A manifold-like portion 70 of the cup-shaped element distributes the vacuum to the various ports, such as ports 62c and 62p to be applied to secure retractor 50 to the heart. An alternative form of the retractor includes a separate hose 72 to transfer vacuum to the manifold 70. Ribs 60 keep heart fat from clogging the vacuum manifold section.

The retractor of the parent disclosure further includes a fine support means for immobilizing selected portions of the heart while permitting non-immobilized portions to move in a manner that continues heart operation. This fine support means includes a plurality of rigid arms 80 each being fixed at one end thereof to anchor 68 and having a heart-attaching element 82 thereon, such as at the outer end thereof. As used herein, the term "rigid" is a relative term and means that the arms are rigid enough whereby the force of the heart won't move them. But they can be adjustable such as being formed of a wire-wound gooseneck or soft metal which allows each arm to be individually shaped according to the needs of the attachment location. The heart-attaching elements can be suction attachment points, such as suction cups that are fluidically connected to manifold 70. Other means of attaching the elements to the heart, can be used as well without departing from the scope of the present disclosure as will occur to those skilled in the art based on the teaching of this disclosure. Examples of other such elements include glue, sutures, clamps, shallow pins, pincers or the like, with attachment points being located on the arm as suitable. The rigid arms secure small or fine areas of the heart in place with respect to gross element 52 while permitting the heart to move as required to continue unabated cardiac output. Support means 50 further includes a plurality of flexible support arms 84 each fixed at one end thereof to anchor 68 and having a heart-attaching element 86 on the outer end thereof. Elements 86 can be suction elements similar to the just-discussed elements 82. Flexible arms 84 can be adjusted to secure the heart in the most advantageous locations whereby the heart can continue to operate without undue restriction.

Therefore, broadly, the overall parent retractor comprises a main support which includes the arms, the hub and a stationary member, such as a table top, the floor or the like; a gross support which includes the apex cup and fine support means which regionally immobilizes portions of the heart while leaving other regions of the heart free to operate in an unabated manner to maintain heart output during the surgical procedure. The fine support means can include the rigid arms as well as the surgery target immobilizing means. In this manner, the heart is supported regionally yet operates to maintain blood flow during coronary surgery.

Referring to FIG. 5, it can be seen that parent retractor 10 includes a surgery target-immobilizing element 100 for immobilizing that exact location of the heart on which surgery is being performed. Element 100 includes a rigid arm 102 fixed at one end 104 to connecting arm 106 of stationary main arm 64 and having a U-shaped target-defining element 108 on the other end. Element 108 includes two legs 110 and 112 connected by a central section 114. As shown in FIG. 5, the target vein 116 being incised at 118 is located between legs 110 and 112. Element 108 is rigid as is arm 102 so target area 118 will be immobile even though the remainder of the heart adjacent to this area will be moving. However, only a small section of the heart will be immobilized and thus should not affect the overall operation of the heart during the operation. The target-immobilizing element can be moved anywhere it is needed by simply loosening clamp 120 and moving arm 102 as necessary.

As was discussed in the parent disclosure, during operation of the heart, the left ventricle is a conical shaped cavity which is narrowest at the apex. It shortens both in length and in diameter during a pumping stroke (contraction). Since the volume of blood displaced is more dependent on the reduction in diameter (square) than the shortening in length (first power), any measure which reduces the shortening of the diameter is very detrimental. Also, the right ventricle is attached to the left ventricle and is considerably thinner and less powerful. Suction attachments to this part of the heart which would impede the shortening of muscle may be poorly tolerated. The invention disclosed and taught herein uses a series of linked attachments to the heart. Attachments which are near the artery to be bypassed are paired on opposite sides of the artery and do not move— they immobilize the artery and therefore the muscle in the target region. A lifting suction is applied at the apex of the heart. If this were the only site of lifting, the heart would be stretched and there would be no diameter left. Thus, no blood could be ejected. However, this invention adds additional heart attaching elements that are attached to the heart to lift it. These attachment points would be mobile in that they could allow the heart to move inward and reduce the diameter and eject blood. The key to the invention is the linking of lifting (both at the apex and around the circumference of the heart) and regional immobilization which stops one part around the circumference from moving and therefore allows easy suturing.

As discussed above, while the parent retractor works well, it can be improved. Referring to FIGS. 6A-28, a system for manipulating a heart during cardiac surgery is shown which has improved operation over the parent retractor.

The heart manipulation system of the present invention utilizes a special suction cup to attach various elements thereof to the beating heart in a manner that permits the heart and the myocardium to move during heart operation without unduly affecting the attachment of the element to the heart. Specifically, the suction cup of the present invention applies suction to the heart surface from a source of suction (not shown, but discussed in the parent disclosure). Suction cup 200 of the present invention is best shown in FIG. 7A which shows a suction cup that is most useful with non-flaccid tissue in which it is easier to make the suction cup conform to the tissue than to force the tissue to conform to the suction cup, and FIG. 7B which shows a suction cup that is most useful with flaccid tissue which is easier to force to conform to the shape of the suction cup. Both suction cups 200 can be compared to a prior art suction cup S shown in FIGS. 6A and 6B. As shown in FIGS. 6A and 6B, prior art suction cup S includes a single chamber C that is fluidically connected to a suction line L and which has a rim R for engaging the surface, such as tissue T, to which suction cup S is attached. Suction pressure is applied over an area A which corresponds to the area of the suction line L. As will be understood by those skilled in the art, if tissue T moves it can move away from rim R thereby breaking the suction being applied to tissue T. Still further, if tissue T moves, it might move into suction line L thereby interfering with application of suction to the tissue, as is indicated in FIG. 6B. This latter situation is likely since the maximum suction force is applied over area A and will tend to distort tissue T in the manner indicated in FIG. 6B. Such distortion also tends to move the tissue away from rim R.

However, suction cup 200 shown in FIGS. 7A and 7B does not have these drawbacks because it includes a plurality of chambers and a means for preventing tissue from interfering with suction being applied thereto. Specifically, suction cup 200 is a multi-section suction cup which includes a first chamber 202 having a flexible rim 204 for engaging the tissue M of a heart, and a second chamber 206 for fluidically connecting first chamber 202 to the source of suction via suction line 208. Second chamber 206 of the suction cup has a size that is different from the size of first chamber 202, and a shoulder 209 is formed at the connection between first and second chambers 202 and 206. A mesh grid element 210 is connected to the suction cup, preferably adjacent to shoulder 209, and spans second chamber 206. Flexible rim 204 is flexible in a plurality of planes to accommodate multiplanar movement of the surface of the beating heart without breaking contact between the surface of the heart and flexible rim 204.

As can be understood from FIGS. 7A and 7B, suction cup 200 will not break suction with tissue T even if the tissue is drawn into the suction cup and a large area of applied suction is maintained due to the large area A' of second chamber 206 vis a vis area A of suction cup S. Thus, suction cup 200 is able to adapt to movement of the heart and movement of the myocardium while maintaining a large suction force on the tissue. This permits smaller amounts of myocardium to be affected by the system of the present invention than even the parent retractor. Since chamber 202 is large, rim 204 can be large and thus its flexibility can be increased over rim R of suction cup S. This permits rim 204 of suction cup 200 to follow movement of tissue T far better than rim R of suction cup S.

Figure 17:
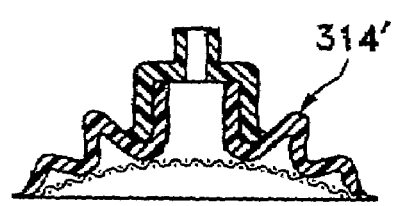
FIG. 17 shows another form of the multisection suction cup.
Figure 16B:
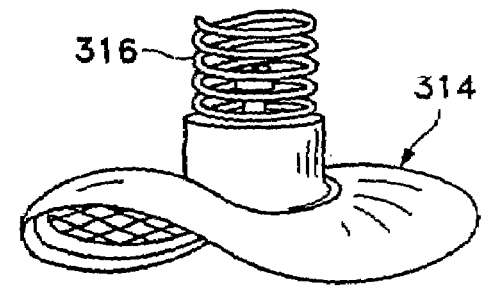

Suction cup 200 is the best mode used in the present invention; however, other forms of suction cups can be used without departing from the scope of the present invention and disclosure. The other forms of the suction cup will also have at least one first chamber and one second chamber and a flexible rim as well as a mesh grid element preventing tissue from interfering with suction applied via the suction cup. Other forms of the suction cup are indicated in FIGS. 17 and 18A through 22B, with FIG. 17 showing a multiplicity of chambers and a multiplicity of shoulders; FIGS. 18A and 18B showing an off center chamber 202'; FIGS. 19A and 19B showing a plurality of suction lines 208' and 208"; FIGS. 20A and 20B showing a reinforcing ring RR surrounding suction line 208'''; FIGS. 21A and 21B showing a ring RR' around a plurality of suction lines; and FIGS. 22A and 22B showing a suction cup 200K having a kidney-shaped perimeter. One or more suction lines can be associated with cup 200K as is indicated in FIG. 22A. Suction cup 200 has walls 200W and 200W1 that are oriented at a sharper angle with respect to base 200B of the suction cup than are the wall W of suction cup S. This permits the walls of cup 200 to be more flexible than the walls of cup S.

Figure 15:
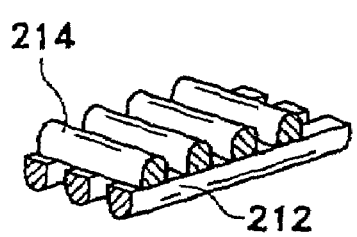
FIG. 15 shows a portion of a preferred form of the mesh means.
Figure 16A:
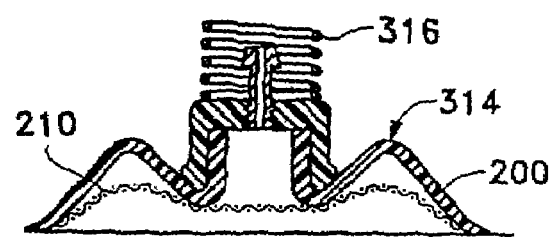
FIGS. 16A and 16B show the flexible multisection suction cup of the present invention.

Mesh grid element 210 functions to preserve suction pressure on the tissue even if the tissue is drawn into the suction cup. Thus, mesh grid element 210 has a first portion that can be engaged by the tissue, and a second portion that will remain open even when the first portion is engaged by tissue. An example of such a mesh grid element is shown in FIG. 15 as including a first portion 212 and a second portion 214 that are arranged orthogonally with respect to each other. Thus, even if tissue engages portion 212, that tissue will be spaced from portion 214 and a fluid passage will remain open between the tissue and the source of suction thereby maintaining suction force on the tissue. Other forms of the mesh grid element can be envisioned by those skilled in the art based on the teaching of this disclosure, and such other forms are also intended to be encompassed by this disclosure.

As will be evident to those skilled in the art based on the teaching of the present disclosure, this flexible rim multi-chamber suction element with a mesh grid element will be used in those elements of the heart manipulation system of the present invention that engage the heart to apply force to the heart to move and manipulate that heart during cardiac surgery.

Figure 11:
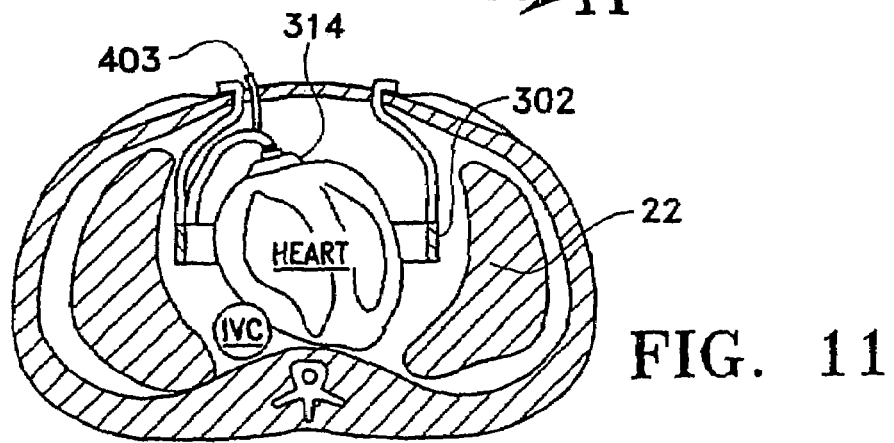
FIG. 11 is a view taken along line 11-11 of FIG. 10.

A heart manipulation system 300 for use in cardiac surgery is broadly shown in FIG. 8 as comprising a frame 302 that, as indicated in FIG. 11, is located within the patient's thoracic cavity during beating heart surgery and which includes means for engaging the pericardial cavity of the patient for mounting said frame on the patient to move with the patient if the patient is moved or re-oriented during surgery.

Frame 302 includes a cross bar 303 that has a multiplicity of teeth 303T thereon for a purpose that will be understood from the following disclosure. Frame 302 further includes means for engaging the patient to support the frame in position in the patient. A preferred form of this means includes two sternal spacers 304 which set the depth of the frame into the chest cavity and keep the frame from twisting as the lungs inflate and which are connected to cross bar 303 by a ratchet-like mechanism 305 that has teeth which engage teeth 303T when the spacers are in the desired location. The frame is expanded inside the pericardial cavity with the cross bar. A handle 305H is operated to set the teeth of the mechanism 305 to teeth 303T. The frame can be either C-shaped or hoop shaped and can be secured to the patient or to an outside stable support. Other anchor means can be used as well as will occur to those skilled in the art based on the teaching of the present disclosure, and these means are intended to be within the scope of this disclosure as well.

As was the case in the parent disclosure, a source of suction is located outside the patient and is used to attach various elements to the patient's heart. Most often, a source of vacuum is from the operating room source which provides approximately 100 to 180 mm of Hg vacuum. The source of suction is not shown herein as those skilled in the art will understand where such source is best located and what source is best suited to the particular application based on the teaching of the present disclosure.

Figure 9:
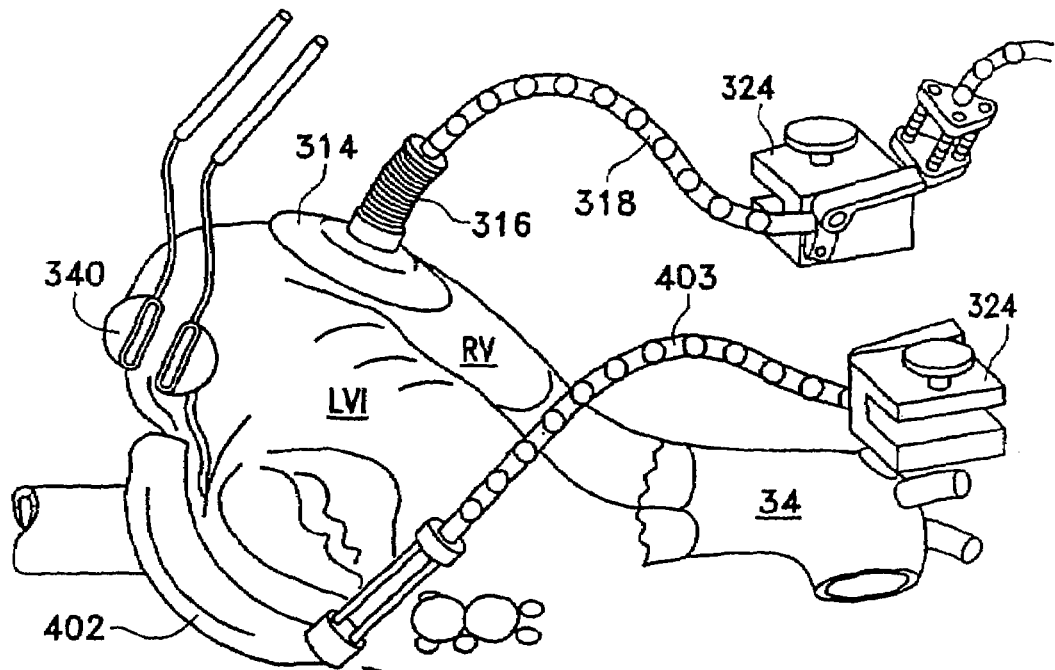
FIG. 9 is an elevational view of the system for manipulating a heart during cardiac surgery in place on a heart.
Figure 10:
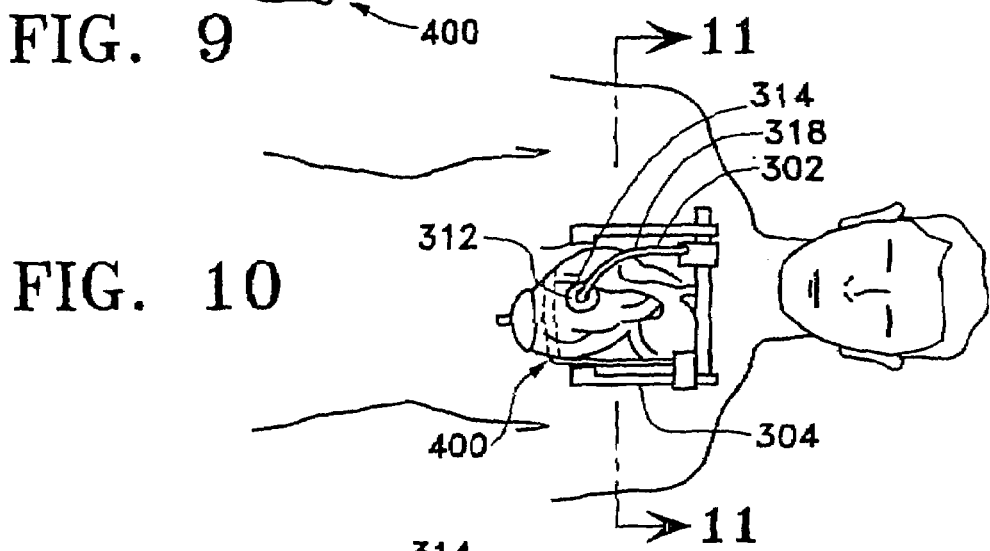
FIG. 10 shows the FIG. 8 retractor in place in a patient.

As shown in FIG. 8, system 300 includes a suspension head mechanism 312 movably mounted on frame 302 for lifting the heart. Mechanism 312 includes a head 314 which engages the heart and which is shown in FIG. 9 as being located near the apical region of the right ventricle to prevent collapse of the right ventricle during manipulation of the heart. As is also shown in FIG. 9, suspension head 314 at least partially overlies the right ventricle. Suspension head mechanism 312 includes a flexible means 316, such as a spring, for connecting flexible head 314 to arm 318 and for permitting multiplanar relative movement between the beating heart and arm means 318 mounting suspension head 314 on frame means 302. Suspension head 314 includes a suction cup such as disclosed above in FIGS. 7A and 7B connected to the source of suction and which includes a flexible rim engaging the myocardium of the heart and being flexible in a plurality of planes so multiplanar movement of the myocardium during operation of the heart will be accommodated by the flexible rim whereby suction applied to the myocardium by the suction cup will not be broken by separation of the myocardium from the suction cup. As discussed above, the suction cup of head 314 includes means, such as the above-discussed mesh grid, for preventing heart tissue from interfering with suction being applied to the myocardium via head 314.

Arm 318 is flexible in one condition as discussed in the parent disclosure, and is made rigid by manipulation of control and anchor element 324. Anchor element 324 includes a base 324A which is movably mounted on cross bar 303 and has internal teeth that engage teeth 303T, and a lever system for locking the internal teeth of element 324 to teeth 303T when desired. A further lever-operated mechanism locks corresponding elements in arm 318 whereby arm 318 is rendered rigid. Arm 318 includes a flexible central line extending from head 314, through flexible element 316 to anchor element 324 and a plurality of relatively movable sections, such as balls 326 interposed between links 328, on the central line. A lever 330 is connected to the central line and when the lever is operated, the elements 326 and 328 are forced together to render the arm rigid. In this manner, the suspension head 314 can be easily maneuvered on a flexible arm into the desired position and then locked into that position by rendering arm 318 rigid. Flexible means 316 permits multiplanar movement of suspension head 314 even after arm 318 is made rigid whereby movement of a beating heart is accommodated by suspension head mechanism 312. When suction is applied to the heart via head 314 the heart will be suspended and can be lifted into the desired position and orientation for cardiac surgery without interrupting cardiac output. The combination of the suction cup, the flexible/rigid arm, the flexible means and the location of the head on the heart effect this result. Various forms of head 314 can be used without departing from the scope of the present invention, and a second form of the head is shown in FIG. 17 as head 314' and which includes a multiplicity of chambers. Any of the suction cup forms shown in FIGS. 16A-22B can also be used for head 314 if desired.

With the heart supported by suspension means 312, the cardiac surgery can be completed if desired. As will be discussed below, however, additional support can be provided. Cardiac surgery was discussed above and in the parent disclosure, reference being made thereto for such discussions. As was discussed, a surgery target immobilizer is used to locally immobilize the heart while permitting the non-engaged portions of the heart to continue to operate so as to maintain cardiac output essentially unabated. Shown in FIG. 23 is a surgery target immobilizer SI discussed in the parent disclosure. Immobilizer SI includes two rigid sections, such as section SIR, each of which includes a plurality of suction cups 200 fluidically connected to a source of suction via a line L to be attached to the heart with the surgical target immobilized for surgery.

The system of the present invention improves this by including a means 340 for locally engaging a selected section of the heart and locally immobilizing the heart adjacent to a surgery target so the heart is supported by the suspension head mechanism and can receive further support from the surgery target immobilizing means and can thus be free to operate during surgery while it is also locally immobilized at the surgery target with non-engaged sections of the heart free to move in a manner whereby essentially unabated cardiac output is maintained while the heart is locally immobilized. The surgery target immobilizing means 340 of the present invention includes a flexible section 342, such as suction cup 200, on each rigid element SIR. The suction cups 200 attached to each rigid element function and operate as discussed above and shown in FIGS. 24 and 25 are connected to the source of suction and each includes a flexible rim engaging the myocardium of the heart and being flexible in a plurality of planes so multiplanar movement of the myocardium during operation of the heart will be accommodated by the flexible rim of the surgery-target immobilizing means whereby suction applied to the myocardium by the suction cup of the surgery target immobilizing means will not be broken by separation of the myocardium from the suction cup of the surgery target immobilizing means. As was discussed above, suction cups of the surgery target immobilizing means each include means for preventing heart tissue from interfering with suction being applied to the myocardium via said suction cup of the surgery target immobilizing means.

As discussed above, in some circumstances, two point support is preferred when performing cardiac surgery. Accordingly, manipulation system 300 of the present invention provides a gross support means 400 movably mounted on frame 300 for engaging the heart to support the heart when the heart is oriented for surgery and which is located at the base of the heart and which cradles the myocardium of the left ventricle along the arterial ventricular groove (AV). Gross support means 400 is shown in FIGS. 8, 9, 12, 13, and 14A-14C. As broadly shown in FIG. 8, gross support means 400 includes a head 402 that is engaged with the heart and which is movably connected to frame 302 by an arm mechanism 403 similar to arm 318 to be flexible and movable with respect to the heart and with respect to frame 302 when desired, and then rendered rigid by operation of a lever 404 of an anchor mechanism 406 that can be located on cross bar 303 or on one of the sternum retractors 304. Operation of the flexible arm 403 is identical to that of arm 318 and thus will not be again discussed.

Gross support means 400 supports the mitral valve annulus to maintain competent mitral valve function and head 402 is placed beneath an infolded section of myocardium. Gross support means 400 includes a handle 408 which is attached to head 402 and which extends outside of the patient during surgery for adjusting the location of gross support means head 402.

Head 402 is shown in FIGS. 12-14C as including a rigid support section 406 connected to a flexible section 488 having malleable rod means 410 received in bores 411 defined in head 402 for retaining a configuration that has been set for head 402 and for connecting head 402 to the arm 403 for mounting gross support means 400 on frame 302. Head 402 can include a plurality of sections which are movable relative to each other and means for maintaining those sections in a selected relative orientation. In this manner, head 402 can be shaped to best support the heart and can be adjusted to meet the needs of an individual heart. As head 314 is also adaptable to the size and shape of an individual heart, the two-point support of system 300 can be adjusted and customized to fit the exact needs of each individual heart. The flexible and adjustable feature of head 402 is indicated in FIG. 13.

Figure 14C:
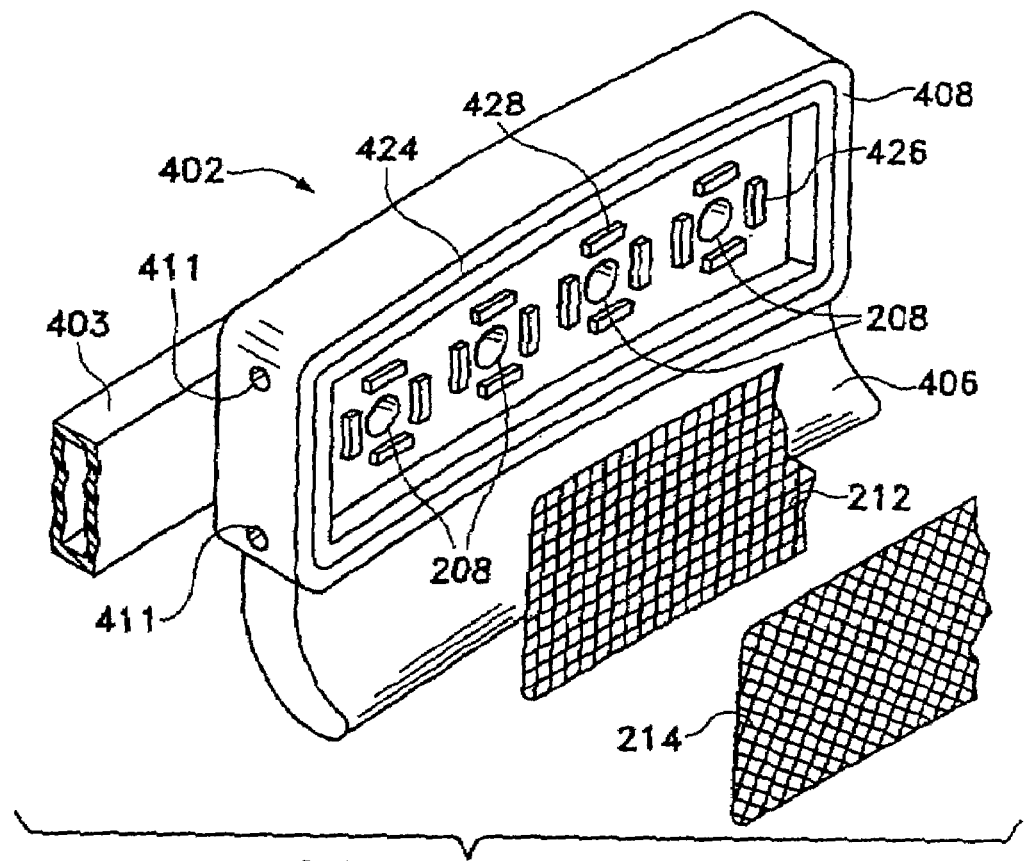
FIG. 14C is an exploded view of the gross support means in larger detail.

As shown in FIGS. 14A-14C, head 402 includes means for applying suction from the source of suction to the heart. AS best shown in FIG. 14A, this means includes a mesh grid means 210 attached to head 402 and spanning a first chamber 420 above a suction applying manifold 422 that is fluidically connected to the source of suction by a suction line for preventing heart tissue from interfering with suction applied by suspension head 402 to the heart. A frame 424 maintains mesh grid means 210 in place on head 402, and ribs, such as rib 426 and rib 428 can be used to maintain the desired position of mesh grid element 210 with respect to suction holes 208 at the end of the suction line.

Using the system 300, a method of performing heart surgery comprises steps of placing frame 300 in the patient, slightly infolding the left atrium of a heart adjacent to the base of the heart, engaging the heart under the edge of the myocardium at the base of the heart with gross support means 400 then using handle 408 tilting and lifting the heart. The heart is engaged near the apex of the heart with suspension head 314 to lift the heart. Such engagement prevents right ventricle collapse. This provides two point support if desired. However, as discussed above, the suspension means alone may be sufficient in some cases to move the heart as necessary. The method can further including a step of using surgery target immobilizing means 340 shown in FIG. 24 to apply suction to the heart adjacent to the selected surgical target for engaging that selected section of the heart and immobilizing that selected section as a surgery target while permitting non-engaged sections of the heart to move and permitting essentially unabated cardiac output to be maintained while the heart is regionally immobilized.

Alternative forms of the frame 302 can be used without departing from the scope of the present disclosure, just so the frame is located to move with the patient. Thus, a frame 302' shown in FIG. 26 can be used. Frame 302' essentially completely surrounds the heart and includes elements 304' for engaging the patient to support frame 302' in place. A handle 302H can be used to adjust the location of frame 302'. Handle 302H includes a knob 302K which operates a pinion system for engaging teeth 303T to adjust the size of the frame circumference as indicated by arrow 302S in FIG. 26.

Figure 27:
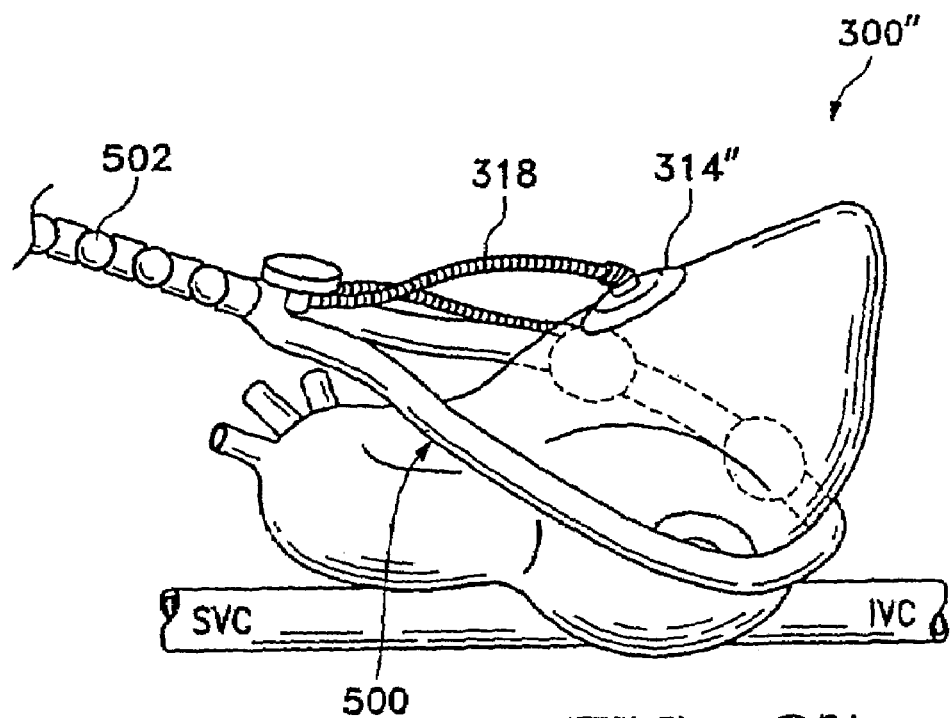
FIG. 27 shows an alternative form of the system for manipulating the heart during cardiac surgery embodying the present invention.
Figure 28:
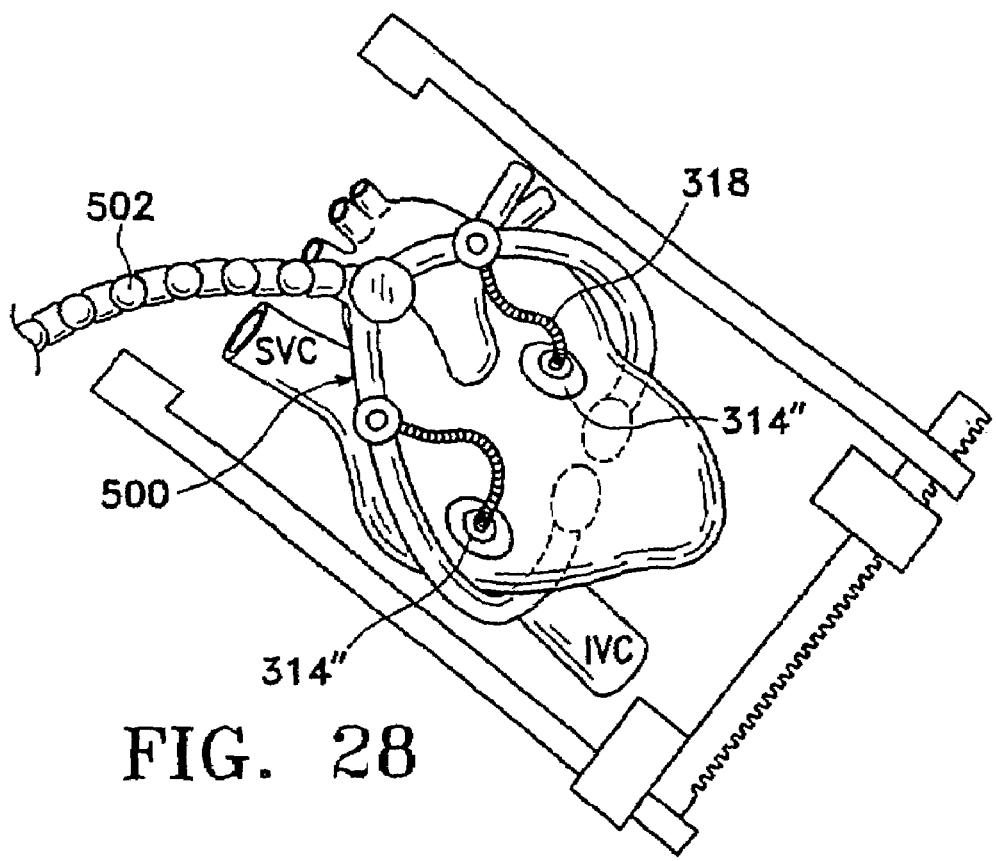
FIG. 28 is a top view of the system shown in FIG. 27.

Yet another form of the manipulation system of the present invention is shown in FIGS. 27 and 28. System 300" includes a gross support system 500 which extends around the heart near the base of the heart and which can include a plurality of suspension heads 314" located at various locations on the heart, including near the apical region and which are connected to flexible/rigid arm 502 which corresponds in structure to arms 318 and 403 discussed above and which are mounted on the frame.

It is understood that while certain forms of the present invention have been illustrated and described herein, it is not to be limited to the specific forms or arrangements of parts described and shown.

We claim:

1. A suction cup adapted to engage a surface of a beating heart with sufficient force to move the beating heart to an unnatural position upon moving the suction cup, while the suction cup maintains engagement with the surface of the heart and the heart continues to beat, said suction cup comprising:
    a first chamber having a flexible rim and configured to engage the surface of the beating heart; and
    a second chamber smaller than said first chamber and fluidly connected therewith at a first end of said second chamber, and a suction line connected in fluid communication with said second chamber, wherein said second chamber provides a separation space between said first chamber and said suction line.

2. The suction cup of claim 1, wherein said suction line is adapted to connect with the source of suction.

3. The suction cup of claim 2, further comprising a reinforcing ring surrounding said suction line at a location where said suction line connects with said second chamber.

4. The suction cup of claim 1, further comprising a shoulder formed by a connection between said first and second chambers.

5. The suction cup of claim 4, further comprising a suction-permeable barrier adjacent to said shoulder and adapted to prevent entry of the surface of the heart into said second chamber.

6. The suction cup of claim 5, wherein said suction-permeable barrier spans said second chamber.

7. The suction cup of claim 5, wherein said suction-permeable barrier comprises a mesh grid element.

8. The suction cup of claim 1, wherein said flexible rim is flexible in a plurality of planes to accommodate multiplanar movement of the surface of the beating heart without breaking contact of said engagement of the flexible rim and first chamber with the surface of the beating heart.

9. The suction cup of claim 1, further comprising a suction-permeable barrier spanning said second chamber, said barrier adapted to prevent entry of the surface of the heart into said second chamber.

10. The suction cup of claim 9, wherein said suction-permeable barrier comprises a mesh grid element.

11. The suction cup of claim 1, further comprising at least one additional chamber fluidly interconnecting said first and second chambers.

12. The suction cup of claim 11, further comprising a plurality of shoulders, each said shoulder formed by a connection between two of said chambers.

13. The suction cup of claim 1, wherein said second chamber is axially offset from said first chamber, such that said first and second chambers are not coaxially aligned.

14. The suction cup of claim 1, comprising a pair of said second chambers fluidly connected with said first chamber.

15. The suction cup of claim 14, wherein each of said second chambers is fluidly connected with a suction line.

16. The suction cup of claim 14, wherein a first of said pair of second chambers is fluidly connected with a first suction line and a second of said pair of second chambers is connected with a second suction line.

17. The suction cup of claim 16, further comprising a reinforcing ring surrounding said first and second suction lines at a location where said suction lines connect with said pair of second chambers.

18. The suction cup of claim 1, wherein said flexible rim is kidney-shaped.

19. A suspension device configured to engage a beating heart and maintain engagement via suction while moving the suspension device to move the beating heart to an unnatural position and maintain the beating heart in the unnatural position to perform a surgical procedure, while the heart continues to beat, said device comprising:
a suction cup having a first chamber configured to engage the surface of the beating heart, and a second chamber smaller than said first chamber and fluidly connected therewith at a first end of said second chamber, and a suction line connected in fluid communication with said second chamber, wherein said second chamber provides a separation space between said first chamber and said suction line; and
a support arm connected to said suction cup and movable therewith to effect movement of the beating heart after engagement of the suction cup to a surface of the beating heart.

20. The suspension device of claim 19, wherein said support arm is configured to lock to a relatively stationary object, into a desired position, to maintain said suction cup and the beating heart in a desired, suspended orientation.

21. The suspension device of claim 20, wherein said support arm is flexibly coupled to said suction cup, permitting multiplanar movement of said suction cup even after locking said support arm into said desired position.

22. The suspension device of claim 19, wherein said support arm is flexibly coupled to said suction cup.

23. The suspension device of claim 19, wherein said support arm is configured to assume a flexible condition for positioning of said suction cup, and a locked position for maintaining a desired position of said suction cup.

24. The suspension device of claim 23, wherein said support arm comprises a plurality of ball members interposed between link members.

25. The suspension device of claim 24, wherein said support arm further includes a flexible line extending through said ball and link members.

26. The suspension device of claim 19, further comprising a suction line extending from said second chamber, said suction line adapted to connect with the source of suction.

27. The suspension device of claim 26, further comprising a reinforcing ring surrounding said suction line at a location where said suction line connects with said second chamber.

28. The suspension device of claim 19, wherein said suction cup further comprises a shoulder formed by a connection between said first and second chambers.

29. The suspension device of claim 28, wherein said suction cup further comprises a suction-permeable barrier adjacent to said shoulder and adapted to prevent entry of the surface of the heart into said second chamber.

30. The suspension device of claim 29, wherein said suction-permeable barrier spans said second chamber.

31. The suspension device of claim 29, wherein said suction-permeable barrier comprises a mesh grid element.

32. The suspension device of claim 19, wherein said suction cup further comprises a flexible rim adapted to engage the surface of the beating heart.

33. The suspension device of claim 32, wherein said flexible rim is flexible in a plurality of planes to accommodate multiplanar movement of the surface of the beating heart without breaking contact of said engagement of the flexible rim with the surface of the beating heart.

34. The suspension device of claim 32, wherein said flexible rim is kidney-shaped.

35. The suspension device of claim 19, wherein said suction cup further comprises a suction-permeable barrier spanning said second chamber, said barrier adapted to prevent entry of the surface of the heart into said second chamber.

36. The suspension device of claim 35, wherein said suction-permeable barrier comprises a mesh grid element.

37. The suspension device of claim 19, wherein said suction cup further comprises at least one additional chamber fluidly interconnecting said first and second chambers.

38. The suspension device of claim 37, wherein said suction cup further comprises a plurality of shoulders, each said shoulder formed by a connection between two of said chambers.

39. The suspension device of claim 19, wherein said second chamber is axially offset from said first chamber, such that said first and second chambers are not coaxially aligned.

40. The suspension device of claim 19, wherein said suction cup comprises a pair of said second chambers fluidly connected with said first chamber.

41. The suspension device of claim 40, wherein each of said second chambers is fluidly connected with a suction line.

42. The suspension device of claim 40, wherein a first of said pair of second chambers is fluidly connected with a first suction line and a second of said pair of second chambers is connected with a second suction line.

43. The suspension device of claim 42, further comprising a reinforcing ring surrounding said first and second suction lines at a location where said suction lines connect with said pair of second chambers.

44. A method of manipulating a beating heart to orient the beating heart in a desired position for performing a surgical procedure, said method comprising the steps of:
providing a suction cup having a first chamber configured to engage the surface of the beating heart, and a second chamber smaller than the first chamber and fluidly connected with the first chamber at a first end of said second chamber, and a suction line connected in fluid communication with said second chamber, wherein said second chamber provides a separation space between said first chamber and said suction line the suction line being further fluidly connected to a source of suction;

contacting a surface of the beating heart with the first chamber;

applying suction between the first chamber and the surface of the beating heart, thereby engaging the suction member with the surface of the beating heart; and moving the suction member while maintaining engagement with the surface of the beating heart, thereby moving the beating heart.

45. The method of claim 44, wherein said moving comprises lifting the beating heart to an elevated position.

46. The method of claim 44, further comprising fixing the suction member in a displaced position to maintain the beating heart in the displaced position for performance of the surgical procedure.

47. The method of claim 44, further comprising providing a suction-permeable barrier between the first and second chambers, thereby preventing the surface of the heart from entering the second chamber during application of suction and engagement by the suction cup.

48. A suspension device configured to engage a beating heart and maintain engagement via suction while moving the suspension device to move the beating heart to an unnatural position and maintain the beating heart in the unnatural position to perform a surgical procedure, while the heart continues to beat, said device comprising:

a suction cup having a first chamber configured to engage the surface of the beating heart, and a second chamber smaller than said first chamber and fluidly connected therewith, said second chamber being further adapted to fluidly connect said first chamber with a source of suction; and a support arm connected to said suction cup and movable therewith to effect movement of the beating heart after engagement of the suction cup to a surface of the beating heart, wherein said support arm is flexibly coupled to said suction cup, permitting multiplanar movement of said suction cup even after locking said support arm into said desired position.

* * * * *